United States Patent [19]

Della Valle et al.

[11] Patent Number: 5,523,294
[45] Date of Patent: Jun. 4, 1996

[54] DI-LYSOGANGLIOSIDE DERIVATIVES

[75] Inventors: Francesco Della Valle, Padua; Aurelio Romeo, Rome, both of Italy

[73] Assignee: FIDIA S.p.A., Abano Terme, Italy

[21] Appl. No.: 89,601

[22] Filed: Jul. 12, 1993

Related U.S. Application Data

[63] Continuation of Ser. No. 557,999, Jul. 26, 1990, abandoned.

[30] Foreign Application Priority Data

Jul. 27, 1989 [IT] Italy ..................... 48247/89

[51] Int. Cl.$^6$ .................... A61K 31/70
[52] U.S. Cl. ................. 514/25; 514/54; 536/4.1; 536/53; 536/55; 536/55.3; 536/124
[58] Field of Search ............. 536/4.1, 53, 55, 536/55.3, 124; 514/54, 25

[56] References Cited

U.S. PATENT DOCUMENTS

| | | | |
|---|---|---|---|
| 4,476,119 | 10/1984 | Della Valle et al. | 514/25 |
| 4,593,091 | 6/1986 | Della Valle et al. | 536/53 |
| 4,713,374 | 12/1987 | Della Valle et al. | 514/54 |
| 4,716,223 | 12/1987 | Della Valle et al. | 536/53 |
| 5,264,424 | 11/1993 | Della Valle | 514/54 |

FOREIGN PATENT DOCUMENTS

| | | |
|---|---|---|
| 0167449 | 1/1986 | European Pat. Off. |
| 0315113 | 5/1989 | European Pat. Off. |
| 0352766 | 1/1990 | European Pat. Off. |
| 0373039 | 6/1990 | European Pat. Off. |

OTHER PUBLICATIONS

CA 111:4544p (1989) Y. Kawano et al.
S. Sonnino et al Biochemistry, vol. 28, No. 1 (1989) pp. 77–84.
M. Tiemeyer et al Journal of Biological Chemistry, vol. 264, No. 3 (1989) pp. 1671–1681.
S. Ladisch et al Journal of Biological Chemistry, vol. 264, No. 20 (1989) 12097–12105.
Y. Hirabayashi et al Journal of Biochemistry, vol. 103, No. 1 (1988) pp. 1–4.
Acta Psychiat. Scand. 55, 102, (1977).
Eur. Medicophys., 13, 1, (1977).
Adv. Exp. Med. Biol. 71, 275 (1976).
Electromyogr. Clin, Neurophysiol. 19, 353, (1979).
Minerva Medica, 69, 3277, (1978).
Minerva Stomat. 27, 177, (1978).
Med. del Lavoro, 68, 296 (1977).
Brain Res. 197, 236, (1980).
J. of Neurochem. 37, 350 (1981).
Glycolipid Methodology, Robert W. Ledeen and Robert K. Yu, pp. 186–215, Chapter IX and X (1976).
Glycolipid Methodology, Eric G. Brunngraber, Guido Tettamanti and Bruno Berra, pp. 158–187, Chapter VIII (1976).
Favaron et al; PNAS (USA) 85:7351–7355 (Oct. 1988).
Hannun et al; Science 243:500–507 (Jan. 27, 1989).
Manev et al; Journal of Pharmacology and Experimental Therapeutics 252(1):419–427 (Jan. 1990).
Neuenhofer et al; FEBS Letters 185(1):112–114 (Jun. 1985).
Meindl et al; Monatsh. Chem. 97:1628–1647 (1966).
Faillard et al; Hoppe–Seyler's Z. Physiol. Chem. 350:7–798–802 (1969).
Sonnino et al; J. Lipid Res. 26(2):248–257 (1985).
Nores et al; Carb. Res. 179:393–410 (1988).
Song et al; Biochem. 28:4194–4200 (1989).

Primary Examiner—Douglas W. Robinson
Assistant Examiner—Kathleen Kahler Fonda
Attorney, Agent, or Firm—Birch, Stewart, Kolasch & Birch

[57] ABSTRACT

N-acyl-N,N'-di-lysogangliosides, N'-acyl-N,N'-di-lysogangliosides and N,N'-diacyl-N,N'-di-lysogangliosides, wherein the acyl groups are derived from an aliphatic acid having from 1 to 24 carbon atoms, substituted by one or more polar groups are disclosed. The acyl-di-lysogangliosides of the invention exhibit an inhibiting action on protein kinase C activation and, thus, can be utilized in therapies for various pathologies of the nervous system. Pharmaceutical compositions and therapeutic utilities for the lysoganglioside derivatives are also disclosed.

41 Claims, No Drawings

DI-LYSOGANGLIOSIDE DERIVATIVES

This application is a continuation of application Ser. No. 07/557,999, filed Jul. 26, 1990, now abandoned.

The present invention concerns new ganglioside derivatives and more precisely N-acyl-N,N'-di-lysogangliosides, N'-acyl-N,N'-di-lysogangliosides and N,N'-diacyl-N,N'-di-lysogangliosides in which the acyl groups are derived from unsubstituted aliphatic acids having from 1 to 24 carbon atoms or from acids of the same type having from 2 to 24 carbon atoms substituted by one or more polar groups chosen from the group formed by:

chlorine, bromine and fluorine;

free hydroxy groups or hydroxy groups esterified with an organic or inorganic acid;

etherified hydroxy groups;

keto, ketal and acetal groups derived from lower aliphatic or araliphatic alcohols;

keto or aldoxy or hydrazone groups optionally substituted by lower alkyl or aralkyl groups;

mercapto groups, free or esterified with a lower aliphatic or araliphatic acid or etherified with lower aliphatic or araliphatic alcohols;

free or esterified carboxy groups;

sulfonic groups, free or esterified with lower aliphatic or araliphatic alcohols;

sulfamide or sulfamidic groups substituted by lower alkyl or aralkyl groups or lower alkylene groups;

sulfoxide or sulfonic groups derived from lower alkyl or aralkyl groups;

nitryl groups;

free or substituted amino groups, and quaternary ammonium derivatives of such amino groups;

at least one of the acyl groups being substituted in the aforesaid manner. The invention also includes the esters and amines of the sialic carboxy groups of said gangliosides, and also inner esters with lactone bonds between the sialic carboxy groups and the hydroxyls, as well as the derivatives peracylated on the ganglioside hydroxyls, both of the acyl-gangliosides themselves and of their functional derivatives. Salts of all of these compounds are also included within the scope of the invention. The term "lysoganglioside" is used in the literature to indicate compounds derived from natural gangliosides by elimination of the acyl group present on the sphingosine nitrogen. Such elimination can be achieved enzymatically, for example by exposing the gangliosides to the action of the glycosphingolipid-ceramide-deacylase enzyme. This type of enzymatic hydrolysis leaves the acyl-amino and acylhydroxy groups in the neuraminic acids intact. In order to deacylate these groups and obtain a ganglioside derivative containing two free amino groups, both on the sphingosine nitrogen and neuraminic nitrogen, it is necessary to use chemical hydrolysis under alkaline conditions. The ganglioside derivatives obtained by deacylation on the neuraminic nitrogen in the aforesaid manner are usually designated in the literature as "de-N-acetyl-gangliosides", the acyl group in this position being mainly the acetyl group. Designating the two nitrogen atoms in the sphingosine and neuraminic residues as "N" and "N'", respectively, the nomenclature "N'-lysogangliosides" can be used for the aforesaid de-N-acetyl-gangliosides, in the same way as the term lysogangliosides is used for derivatives having the free amino group in the sphingosine residue, which should therefore be more precisely identified as "N-lysogangliosides". The term "N,N'-di-lysogangliosides" on the other hand refers to the compound with both free amino groups. This nomenclature will be used in the present specification.

Gangliosides are generally mixtures of various unitary chemical compounds, identifiable by an approximate formula such as

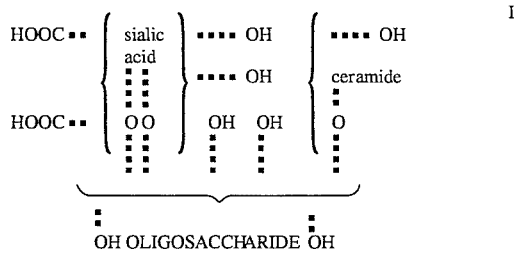

including one oligosaccharide part, generally chemically well defined for each ganglioside, one sialic part (that is, constituted by one or more sialic acids) and one ceramide part, these three parts generally being constituted by a mixture of various sialic acids and various ceramide residues. Sialic acids are acylated derivatives of neuraminic acid of the formula

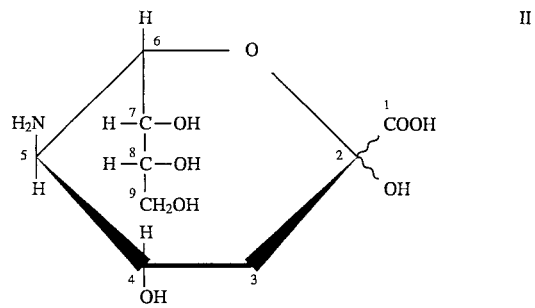

in which the amino group is acylated with acetic or glycolic acid and the hydroxyl groups can also be esterified with these acids.

The ceramide group represents an N-acylsphingosine corresponding to one of the two formulae

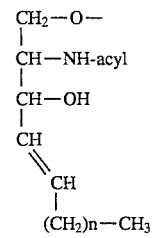

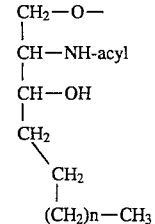

in which n=6–18 and the acyl is derived from a saturated or unsaturated fatty acid with 16 to 22 carbon atoms or from a corresponding hydroxy-acid.

As already noted above, in gangliosides the sialic and ceramide residues are mixtures of groups with the aforesaid formulae, and this is also true of the purified gangliosides described in the literature. The number of sialic acids present in gangliosides usually varies between 1 and 5. The sialic residues are bound to the oligosaccharide by a ketose bond formed by the hydroxyl in the 2-position with a hydroxyl of the oligosaccharide.

When several sialic acids are bound together, their molecules are united by ketose bonds formed between the hydroxyls of positions 2 and 8 of two sialic acid molecules. The sialic acids of gangliosides, including those which are purified as described above, are mixtures of various chemically unitary acids, for example N-acetylneuraminic acid and N-glycolylneuraminic acid, in which the former is predominant, and possibly one or more of their O-acyl derivatives, for example 8-O-acyl derivatives. The oligosaccharide is composed of a maximum of 5 monosaccharides or derivatives of the same with an acylamino group, especially hexoses and their derivatives of the aforesaid type. There is however at least one glucose or galactose molecule always present in the oligosaccharide; the most frequent residue as the acylamino derivative of the aforesaid sugars is N-acetylglucosamine and also N-acetylgalactosamine.

The aforesaid definition of the derivatives according to the invention includes the group of ganglioside derivatives which present an unsubstituted aliphatic group on the neuraminic nitrogen and an aliphatic group substituted by polar groups on the sphingosine nitrogen. Should the aforesaid acyl group on the neuraminic nitrogen be acetyl, the scope of the present invention is extended to those compounds which predominantly contain such acetyl groups, mixed with the glycol group and with acyl groups also present on the hydroxyls, as in natural gangliosides. The term "N-lysogangliosides" or "N-acetyl-(N)-lysogangliosides" will be used in the following description of the invention both for these derivatives which will be characterized as "natural" (for example, natural N-dichloroacetyl-N-lyso $GM_1$), and for those which possess a unitary acetyl group on the neuraminic nitrogen, which will be designated without this addition or preferably as derivatives of N,N'-di-lysogangliosides, for example N-dichloroacetyl-N'-acetyl-N,N'-di-lyso $GM_3$. The term "acyl-di-lysogangliosides" will however hereafter be used also to signify all the new compounds of the invention. As will be discussed hereafter, it is possible to selectively deacylate a ganglioside on the nitrogen and on the hydroxy groups of the neuraminic acid alone, for example with a dilute alkaline hydroxide. By acylating the amine group of the neuraminic residue in these compounds with an acyl other than the acetyl (and glycolyl), N,N'-diacyl-N,N'-di-lysogangliosides are obtained which also conserve a natural part of gangliosides, and that is the mixed acyl group derived from higher aliphatic acids. Such derivatives, which constitute a preferential group of the new compounds according to the present invention, will be designated as N'-acyl-N'-lysogangliosides, for example N'-dichloroacetyl-N'-lyso $GM_1$, N'-methoxyacetyl-N'-lyso $GM_3$, N'-difluoroacetyl-N'-lyso $GM_1$, etc.

The new compounds of the present invention are semi-synthetic analogues of gangliosides and differ from them primarily because of the presence of unitary and well defined acyl groups on the sphingosine and/or neuraminic nitrogen (with the exception of natural N-acyl-lysogangliosides) and because of the fact that of the acyl groups present, at least one is substituted by polar functions and in other cases because of the unsubstituted aliphatic acyl groups being lower (superior) or higher (superior) homologues of the acyl groups on the sphingosine nitrogen and on the neuraminic nitrogen, respectively, of the gangliosides. According to the present invention, the aforesaid new compounds have pharmacological actions similar to those of natural gangliosides. Included in the invention are also pharmaceutical preparations containing one or more of the novel derivatives of di-lysogangliosides or of their functional derivatives or respective salts or of their mixtures, as well as the therapeutic use and procedures for their preparation.

The di-lysogangliosides which serve as basis for the preparation of the novel N,N'-diacyl derivatives according to the present invention are primarily those obtainable by deacylation of gangliosides extractable from natural products, and particularly from tissue of the central or peripheral nervous systems of vertebrates, but also from the adrenal marrow, from erythrocytes, from the spleen or other organs. They can be purified gangliosides, as are defined by this term in the literature for those identifiable by a unitary structure with respect to the saccharide part, or they may be ganglioside mixtures.

Examples of the most important gangliosides to be used as starting base for the new derivatives, are those in which the oligosaccharide is formed by a maximum of 4 hexose residues, and in which this saccharide part is chemically unitary. The hexoses are preferably chosen from the group formed by N-acetylglucosamine and N-acetylgalactosamine (ganglioside group A). The gangliosides of this group are for example those extracted from vertebrate brain, such as those described in the article "Gangliosides of the Nervous System" in "Glycolipid Methodology", Lloyd A., Witting Ed., American Oil Chemists Society, Champaign, Ill. 187–214 (1976) (see especially Table 1), for example the gangliosides $GM_4$, $GM_3$, $GM_2$, $GM_1$-GlcNAc, $GD_2$, $GD_{1a}$-GalNAc, $GT_{1c}$, GQ, $GT_1$ and, in particular, those in which the oligosaccharide contains at least one residue of glucose or galactose and one of N-acetylglucosamine or N-acetylgalactosamine and especially the following (ganglioside group B):

$GM_1$

Gal(1→3)GalNAC(1→4)Gal(1→4)Glc(1→1) Ceramide

NANA $GD_{1a}$

Gal(1→3)GalNAC(1→4)Gal(1-43 4)Glc(1→1) Ceramide

 

NANA     NANA $GD_{1b}$

Gal(1→3)GalNAC(1→4)Gal(1→4)Glc(1→1) Ceramide

NANA

NANA

GT$_{1b}$

Gal(1→3)GalNAC(1→4)Gal(1→4)Glc(1→1) Ceramide

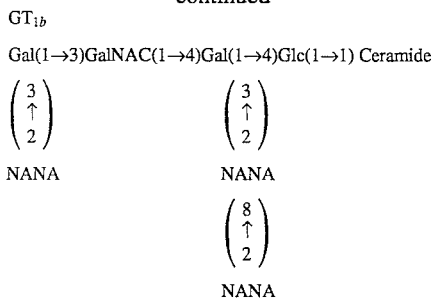

where Glc stands for glucose, GalNAc stands for N-acetylgalactosamine, Gal stands for galactose, and NANA stands for N-acetylneuraminic acid.

To better illustrate the structure of the gangliosides of the aforesaid formula I, which is substantially the same as for the derivatives of the present invention, and in particular the character of the bonds between the saccharide part, the sialic acids and the ceramide, there is reproduced here in its entirety the formula of a "pure" ganglioside GM$_1$ containing only one sialic acid (represented by N-acetylneuraminic acid or N-glycolylneuraminic acid).

substituted with one of the aforesaid acyl groups. They can be obtained according to the procedure of the present invention by deacylation of the ganglioside mixtures and subsequent reacylation, optionally, after reacylation of other groups deacylated in the sialic part of the gangliosides. Among the most important ganglioside mixtures to be used as starting products are ganglioside extracts obtained from the nervous system, in particular from the brain and containing the aforesaid gangliosides GM$_1$, GD$_{1a}$, GD$_{1b}$ and GT$_{1b}$.

It is known that gangliosides play an important role in the nervous system and it has recently been demonstrated that gangliosides are useful in therapy for pathologies of the peripheral nervous system and in pathologies of the central nervous system [Acta Psychiat. Scand., 55, 102, (1977); Eur. Medicophys., 13, 1, (1977); Ric. Sci. Educ. Perm. Suppl. 9, 115, (1978); Adv. Exp. Med. Biol. 71, 275, (1976); Electromyogr. Clin. Neurophysiol., 19, 353, (1979); Minerva Medica, 69, 3277, (1978); Minerva Stomat., 27, 177, (1978); Med. del Lavoro, 68, 296 (1977); Brain Res. 197, 236, (1980)].

The therapeutic action of gangliosides seems to consist mainly in stimulating sprouting phenomena of nerve cells and in activating the membrane enzymes implicated in the

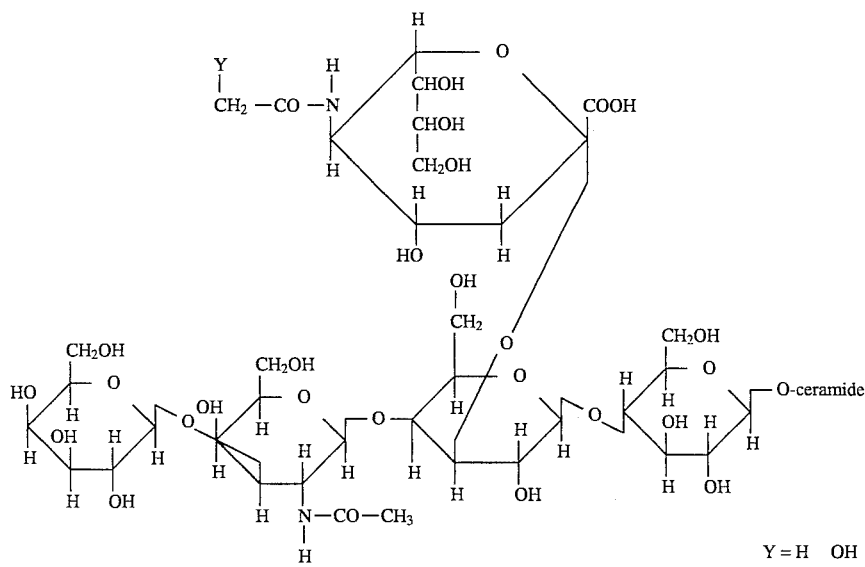

The same formula is essentially valid also for a derivative of ganglioside GM$_1$ according to the present invention, wherein the ceramide residue is substituted with a corresponding "artificial" ceramide and in which its acyl group is derived from one of the aforesaid aliphatic acids substituted by polar groups and also the Y—CH$_2$—CO group on the neuraminic nitrogen is substituted by an acyl group derived from such acids.

Included in the present invention are also the mixtures of the new N,N'-diacyl-di-lysogangliosides and in particular those which are derived from ganglioside mixtures such as are present in the extracts of various animal tissues, such as in "total" extracts, or in different fractions, for example those described in the literature. Such mixtures are described, for example, in the aforesaid Witting reference, in "Extraction and analysis of materials containing lipid bound sialic acid" in the aforesaid Witting book, pages 159–186 (1976), in "Gangliosides of the Nervous System", same book, pages 187–214, and in German Patent 25 49 680. In these new mixtures the N-acyl part of the ganglioside mixtures is conduction of nervous stimuli, such as the enzyme (Na$^+$, K$^+$) ATPase [Brain Res., 197, 236 (1980), J. of Neurochem. 37, 350 (1981)]. Neuronal sprouting stimulated by gangliosides enhances the functional recovery of damaged nervous tissue.

Further studies have been carried out to find compounds which could prove more efficient than gangliosides in therapy for nervous system pathologies. These studies have led for example to the discovery that inner esters of gangliosides, in which one or more hydroxyls of the saccharide part are esterified with one or more carboxy groups of the sialic acids (intramolecular reaction) with the formation of the same number of lactone rings, which are more active than gangliosides themselves in enhancing neuronal sprouting and in activating the membrane enzymes implicated in the conduction of nervous stimuli, such as the enzyme (Na$^+$, K$^+$) ATPase (see for example U.S. Pat. No. 4,476,119, U.S. Pat. No. 4,593,091 and U.S. Pat. No. 4,716,223).

An improved activity on neuronal sprouting and the conduction of nervous stimuli are also presented by the "outer" esters of gangliosides, that is, esters of the carboxy functions of sialic acids with various alcohols of the aliphatic, araliphatic, alicyclic or heterocyclic series. The amides of gangliosides also possess the same property, as well as the peracylated derivatives both of amides and esters, or of simple gangliosides. All of these derivatives, which are described in U.S. Pat. No. 4,713,374, are also to be considered basic substances for the new N-acylated derivatives of the present invention. At the basis of the present invention is the discovery that the new acyl-di-lysogangliosides and their aforesaid functional derivatives or their salts possess essentially the same pharmacological actions as natural gangliosides or their analogous functional derivatives, with a range of action which is modified in respect to many parameters, such as onset rate, duration and intensity of the sprouting action of neuronal cells. This range of action can be regulated according to the greater or lesser lipophilic or hydrophilic character of the acyl component, or the type and degree of side effects, which can in some cases be positive or negative according to the therapeutic problem to be tackled, such as above all the inhibiting activity of protein kinase C. In many cases it is possible to use the new derivatives to exploit the action of acids corresponding to a certain acyl group, bypassing the specific action of the ganglioside part, which in such cases has the function of a vehicle. Such is the case, for example, of the new compounds according to the invention, in which N- and N'-acyl groups are derived from an acid which has an action on the central or peripheral nervous system, such as γ-aminobutyric acid. The new acyl-di-lysogangliosides of the present invention can therefore be used instead of natural products or their already known semisynthetic derivatives and they are valuable surrogates in cases where patients do not respond satisfactorily to treatment with conventional products or in cases presenting individual peculiarities or allergies. As already mentioned, they can be used as vehicles because of the specific pharmacological action of the acid corresponding to the N-acyl group. The aforesaid pharmacological properties of the new N,N'-diacyl-di-lysogangliosides can be illustrated by the following experiments conducted in vitro on N,N'-di-dichloroacetyl-di-lyso $GM_1$.

Ability of N,N'-di-dichloroacetyl-di-lyso $GM_1$ and $GM_1$ to stimulate nervous regeneration measured in terms of sprouting activity Formation of neurites from N2A neuroblastomi cells N2A cells are seeded in a culture medium constituted by DMEM+ 10% of fetal calf serum. 24 hrs later the culture medium is substituted by an equal volume of the same medium containing the compound to be studied.

Each compound is first dissolved in chloroform/methanol, and then the solution is deprived of solvent and redissolved in the culture medium to a final concentration of 50 µM and 100 µM.

Ganglioside $GM_1$ is used for comparison. The cultures are examined after 24 hrs for cells presenting neurites.

| | |
|---|---|
| CONTROLS | 3 ± 2% |
| $GM_1$ (100 µM) | 77 ± 8% |
| N,N'-di-dichloroacetyl di-lyso $GM_1$ (100 µM) | most cells are detached |
| N,N'-di-dichloroacetyl di-lyso $GM_1$ (50 µM) | 82 ± 8% |

The di-lyso compounds at the highest concentration cause the cells to become round and detached, but do not cause their destruction. At a concentration of 50 µM, however, the di-lyso compounds produce longer and more elaborately branched neurites than at 100 µM of $GM_1$.

Ability of N,N'-di-dichloroacetyl-di-lyso $GM_1$ and $GM_1$ to antagonize glutamate-induced neurotoxicity in primary cerebral granule cells Embryonic granular cells from the cerebellum are used after 8 days' incubation in vitro. The cultures are washed with Locke's solution, pretreated for 15 minutes with N,N'-di-dichloroacetyl-di-lyso $GM_1$ and for 2 hrs with $GM_1$, then washed three times with medium containing serum. Locke's solution without Mg+2 is added at room temperature for 15 minutes. 24 hrs later the MTT test is effected to establish cell survival.

| Treatment | MTT (Yield relative to staining) |
|---|---|
| Controls | 100% |
| Glutamate | 0% |
| Glutamate + $GM_1$ (100 µM) | 98% |
| Glutamate + N,N'-di-dichloroacetyl -di-lyso $GM_1$ (5 µM) | 88% |

MTT = 3-(4,5-dimethyltriazol-2-yl)-2,5-diphenyltetrazolium bromide (MTT): only viable cells are stained (maximum value 100 = yellow staining)

The acyl-di-lysogangliosides of the present invention and their functional derivatives generally possess neurotoxic qualities at doses far higher than active doses and a neuroprotective action at concentrations about 20 times lower than those used for $GM_1$.

Because of the aforesaid pharmacological properties, the derivatives of the present invention can be used as drugs in the following pathologies, cerebral ischemia, metabolic encephalopathies such as hypoglycemia and hypoxia, toxic encephalopathies, trauma, aging, epilepsy, neurodegenerative diseases such as Parkinson's disease and Huntington's chorea, and mental disorders.

All of the aforesaid derivatives of the new acyl-di-lysogangliosides of the invention, i.e., esters, inner esters, amides and peracylates, can be obtained by the procedures described in the aforesaid patents for the corresponding ganglioside derivatives. The invention also includes in particular mixtures of these derivatives, such as are obtained from mixtures of acyl-di-lysogangliosides according to the invention, which are in turn obtained from the aforesaid ganglioside mixtures.

The ester groups of the new N,N'-diacyl-di-lysoganglioside derivatives are derived particularly from alcohols of the aliphatic series and especially from those with a maximum of 12 and especially 6 carbon atoms, or of the araliphatic series with preferably one single benzene ring optionally substituted by 1–3 lower alkyl groups ($C_{1-4}$), for example methyl groups, and a maximum of 4 carbon atoms in the aliphatic chain, or from alcohols of the alicyclic or aliphatic alicyclic series with one single cycloaliphatic ring and a maximum of 14 carbon atoms or of the heterocyclic series with a maximum of 12 and especially 6 carbon atoms and only one heterocyclic ring containing a heteroatom chosen from the group formed by N, O and S. The amide groups of the carboxy function in the acyl-di-lysoganglioside derivatives of the present invention are derived from ammonia or from amines of any class with preferably a maximum of 12 carbon atoms. The aforesaid alcohols and amines can be unsubstituted or substituted, especially by functions chosen from the group formed by hydroxy, amino and alkoxy groups with a maximum of 4 carbon atoms in the alkyl, carboxy or carbalkoxy with a maximum of 4 atoms in the alkyl residue, alkylamino or dialkylamino with a maximum of 4 carbon atoms in the alkyl groups, and can be saturated or unsaturated, especially with a single double bond.

The alcohols which are used to esterify the carboxy functions of the acyl-di-lysogangliosides according to the present invention can be monovalent or polyvalent, in particular bivalent. Of the alcohols of the aliphatic series special mention should be made of the lower alcohols with a maximum of 6 carbon atoms, such as methyl, ethyl, propyl and isopropyl alcohol, n-butyl, isobutyl and tert-butyl alcohol, and of the bivalent alcohols such as ethylene glycol and propylene glycol. Of the alcohols of the araliphatic series special mention should be made of those with only one benzene residue, such as benzyl alcohol and phenethyl alcohol; of the alcohols of the alicyclic series, preference should be given to those with only one cycloaliphatic ring, such as cyclohexyl alcohol (cyclohexanol), or terpene alcohols such as menthanol or carvomenthol, or one of the terpineols or terpinenols or piperitol.

Of the alcohols of the heterocyclic series, special mention should be made of tetrahydrofuranol or tetrahydropyranol.

To esterify the carboxy groups of acyl-di-lysogangliosides it is possible to also use aliphatic alcohols, substituted for example by amino functions, such as aminoalcohols, for example those with a maximum of 4 carbon atoms and especially amino alcohols with a dialkyl($C_{1-4}$)-amino group such as diethylaminoethanol. The carboxy amide functions according to the present invention are either derived from ammonia (and the amide in this case is the unsubstituted amide —$CONH_2$) or by primary or secondary amines, especially by those containing a maximum of 12 carbon atoms. Such amines can be of an aromatic, heterocyclic or alicyclic nature, but particularly aliphatic. A preferred object of the present invention are the carboxy amide derivatives of aliphatic amines with a maximum of 12 carbon atoms, the amines of which can be open-chained, straight-chained or branched or can be cyclic, such as for example alkylamines derived from alkyls with between 1 and 6 carbon atoms, such as methylamine, ethylamine, propylamine, hexylamine, dimethylamine, diethylamine, diisopropylamine and dihexylamine, or the alkylene amines derived from alkylene groups with straight chains with between 3 and 6 carbon atoms or corresponding chains substituted by between 1 and 3 methyl groups such as pyrrolidine, piperidine or azepine. The alkyl or alkylene groups of these amines can also be interrupted in the carbon atom chain or substituted by other hetero-atoms, in particular by nitrogen atoms, and the amides of the invention are derived in this case from diamines, such as for example ethylenediamine, trimethylenediamine or piperazine; or should the alkyl or alkylene groups be interrupted or substituted by oxygen or sulfur atoms, the amides represent aminoalcohol derivatives, such as aminoethanol or aminopropanol or they are derived from morpholine or thiomorpholine. An especially interesting feature of the present invention are the esters and amides specified above of acyl-di-lysogangliosides derived from gangliosides of the aforesaid groups A and B, and of their mixtures. The invention also includes derivatives peracylated in the hydroxyls of the saccharide part, the sialic acids and the ceramide of the esters and amides described herein. In these derivatives the acyl groups can be derived from acids of the aliphatic, aromatic, araliphatic, alicyclic or heterocyclic series; they are formed preferably from acids of the aliphatic series with a maximum of 10 carbon atoms and especially 6 carbon atoms, for example formic, acetic, propionic, butyric, valerianic (valeric), capronic or caprinic acid. They may also be derived from acids for example with the same number of carbon atoms but substituted, particularly by hydroxy acids such as lactic acid, by aminoacids such as glycine or by dibasic acids such as succinic, malonic or maleic acids.

Of the aromatic acids should be mentioned those with only one benzene nucleus, particularly benzoic acid and its derivatives with methyl, hydroxy, amino or carboxy groups, such as p-aminobenzoic acid, salicylic acid or phthalic acid.

The invention also includes the peracylated derivatives of acyl-di-lysogangliosides and their aforesaid mixtures, with however free carboxy functions. Of these derivatives, particularly important are those acylated derivatives derived from the acids specified herein.

One group of new derivatives to be mentioned is the one constituted by acyl-di-lysogangliosides which are esterified or converted into amides or which are peracylated on the hydroxy groups, the ester groups of which are derived from saturated aliphatic alcohols with a maximum of 6 carbon atoms and unsubstituted or substituted by hydroxy, alkoxy groups with a maximum of 4 carbon atoms, amino, alkylamino or dialkylamino groups with a maximum of 4 carbon atoms in the alkyl groups, carboxy groups, carbalkoxy groups with a maximum of 4 carbon atoms in the alkyl residue, or by the corresponding alcohols with one double bond at the most, by araliphatic alcohols with only one benzene ring, unsubstituted or substituted by 1 to 3 metal groups, by cycloaliphatic or aliphatic-cycloaliphatic alcohols with a ring or cyclohexane unsubstituted or substituted by 1 to 3 methyl groups and a maximum of 4 carbon atoms in the aliphatic part, by tetrahydrofuranol or by tetrahydropyranol. Such compounds also include those in which the amide groups are derived from ammonia or from alkylamines, dialkylamines or alkylene amines with a maximum of 6 carbon atoms in the alkyl groups and from 4 to 8 carbon atoms in the alkylene groups and in which the alkyl or alkylene groups can be interrupted in the carbon atom chain by heteroatoms chosen from the group formed by nitrogen, oxygen and sulphur, the amino group being possibly —NH— in the presence of a nitrogen atom substituted by an atkyl with a maximum of 4 carbon atoms and/or they can be substituted by moieties chosen from the group formed by amino groups, alkylamino or dialkylamino groups with a maximum of 4 carbon atoms in the alkyl groups, or by hydroxy or alkoxy groups with a maximum of 4 carbon atoms in the alkyl groups, or by araliphatic amines with only one benzene ring optionally substituted by a maximum of 3 methyl groups and with a maximum of 4 carbon atoms in the aliphatic part, and in which the acyl groups esterifying the hydroxyls are derived from aliphatic acids, saturated or unsaturated, with a maximum of 6 carbon atoms, which also can be substituted by a function chosen from the group formed by hydroxy, amino and carboxy groups. Salts of these derivatives are also included within the scope of the invention.

The unsubstituted aliphatic acids from which one of the acyl groups in the new derivatives of the invention may be derived have preferably from 1 to 11 carbon atoms, are preferably saturated, straight-chained or branched, such as for example formic acid, acetic acid, propionic acid, the butyric acids, the valerianic acids, such as especially normal-valerianic acid and iso-valerianic acid, trimethylacetic (pivalic) acid, capronic acid and isocapronic acid, enanthic acid, caprylic acid, pelargonic acid, caprinic acid, undecylic acid, di-tert-butylacetic acid and 2-propylvalerianic acid. Of the unsaturated acids there should be mentioned angelic acid and tiglic acid. Of those acids with longer chains and a higher number of carbon atoms, up to 24, should be mentioned especially those with straight chains and particularly those with 12 to 16 carbon atoms, for example lauric acid, myristic acid and palmitic acid, and those with even larger carbon contents such as oleic acid, elaidic acid, stearic acid, eicosancarbonic acid and behenic acid.

In the branched-chain acyl groups, both those with a lower number of carbon atoms (such as $C_{1-11}$), and those having from 12 to 24 carbon atoms, the lateral chains are preferably lower alkyls with a maximum of 4 carbon atoms, especially methyl groups.

Acyl radicals substituted by polar groups are preferably those with 1 to 3 polar groups which can be the same or different from each other. Preference is given to compounds with acyl radicals substituted in the α-position, especially those with a larger content of carbon atoms and/or those which are unsaturated. The aforesaid polar groups are free functions, such as hydroxy or amino groups, or functional derivatives, such as esters, ethers, ketals, etc. The esters, for example, of hydroxy groups, can be derived from acids of the aliphatic, aromatic, araliphatic, alicyclic or heterocyclic series. Such ester groups are preferably derived from therapeutically acceptable acids. The aliphatic acids are preferably lower acids with a maximum of 8 carbon atoms, such as acetic, propionic, butyric or valerianic acids, for example isovalerianic acid or their substituted derivatives, such as hydroxy acids, for example glycolic acid, α- or β-hydroxybutyric acid and lactic acid, amino acids such as natural amino acids, e.g., glycine, alanine, valine and phenylglycine, or dibasic acids, these also optionally being substituted, such as malonic, succinic, maleic and malic acid. Acids of the aromatic series include, for example, benzoic acid or its derivatives substituted by 1 to 3 lower alkyl groups, hydroxyl, or lower alkoxy groups, or by halogens, such as chlorine, fluorine or bromine. Of the araliphatic alcohols should be mentioned above all those with only one benzene ring, such as phenylacetic or phenylpropionic acid, optionally substituted in the aforesaid manner. Alicyclic acids are preferably those with rings having 5 or 6 carbon atoms, for example cyclohexanecarbonic acid or cyclohexanedicarbonic acid. Of the acids of the heterocyclic series can be mentioned especially the simple ones with only one heterocyclic group, such as the derivatives of pyridine or piperidine such as nicotinic acid or isonicotinic acid or α-pyrrolidinecarbonic acid.

The etherified hydroxy groups can be derived from the same alcohols as mentioned previously with regard to esterified sialic groups. Preference is given to groups etherified with aliphatic alcohols having a maximum of 4 carbon atoms or araliphatic alcohols having a maximum of 4 carbon atoms in the aliphatic part and a benzene group optionally substituted as described previously.

The substituted amino groups also can be those derived from the aforesaid amines with regard to the amide groups of sialic acids. Preference is given to amino groups substituted by alkyl groups with a maximum of 4 carbon atoms or aralkyl groups with a maximum of 4 carbon atoms in the aliphatic part and a benzene group optionally substituted as described above. The substituted amino group can however also be an acylated amino group, for example with one of the acids mentioned before with regard to esterified hydroxy groups, and particularly with an aliphatic acid having a maximum of 4 carbon atoms. The aliphatic or araliphatic hydrocarbyl groups described as "lower" in the aforesaid definition of the invention and regarding the substitution of keto, aidehyde, alkoxy, mercapto, sulfonic, sulfamidic, sulfone and sulfoxide groups are groups with a maximum of 8 carbon atoms, preferably between 1 and 4, and also hydrazone groups derived from such hydrocarbyl groups or they are phenylhydrazone groups.

Esterified carboxy groups as possible polar substitutes of N-acyl groups according to the present invention can be those described previously with regard to the esters of the sialic groups of the ganglioside derivatives, but they are derived preferably from alcohols of the aliphatic series with a maximum of 8 carbon atoms and especially with 4 carbon atoms.

Of the lower saturated acids with the aforesaid number of carbon atoms, from which the N-acyl group is derived, preferred are those which are halogenated and especially those which are chlorinated or fluorinated, especially those which are chlorinated in the 2-position. These include, for example, dichloroacetic acid, trichloroacetic acid and its fluorinated or brominated analogues, 2,2-dichloropropionic acid, 2,3-dichloropropionic acid, 2,2,3-trichloropropionic acid, normal-2,2-dichlorobutyric acid, 2,2-dichlorovalerianic acid, 2-chloroisovalerianic acid, 2,3-dichlorovalerianic acid, pentafluoropropionic acid, 3,3-dichloropivalic acid, 3-chloro-2,2-dimethylpropionic acid, chloro-difluoroacetic acid, 2,2-dichlorocapronic acid, 2-monochloropropionic, normal-2-monochlorobutyric, 2-monochlorovalerianic, and 2-monochlorocapronic acids and the fluorinated or brominated analogues of these acids, 2-chloropalmitic acid, 2-chlorostearic acid, 2-chlorooleic acid, 2-chlorolaurinic acid, 2-chlorobehenic acid, 4-chlorophenoxyacetic acid, 2-hydroxypropionic acid (lactic acid), 3-hydroxypropionic acid, 2-hydroxybutyric acid, 2-hydroxyvalerianic acid, 3-hydroxyvalerianic acid, 2,3-dihydroxybutyric acid and 2,3-dihydroxyvalerianic acid or their ethers with lower aliphatic alcohols having a maximum of 4 carbon atoms or their esters on the hydroxy groups with lower aliphatic acids having a maximum of 4 carbon atoms, or with one of the aforesaid acids of the aromatic, araliphatic, alicyclic or heterocyclic series, methoxyacetic acid, 12-hydroxystearic acid, 2-(4-hydroxyphenoxy) propionic acid, 2-hydroxyisocapronic acid, 2-hydroxyisobutyric acid, 4-fluoro-phenoxyacetic acid, hetoxyacetic acid, pyruvic acid, acetacetic acid, levulinic acid and its ketals with lower aliphatic alcohols having a maximum of 4 carbon atoms and/or their oximes or oximes substituted by alkyl groups with a maximum of 4 carbon atoms, mercaptoacetic, 2-mercaptopropionic, 2-mercaptobutyric and 2-mercaptovalerianic acids and their ethers with lower aliphatic monovalent alcohols having a maximum of 4 carbon atoms or their esters with lower aliphatic acids having a maximum of 4 carbon atoms, 2-mercaptolaurinic, oleic and palmitic acids and their esters or ethers of the aforesaid acid type, malonic acid, glutaric acid, monomethylglutaric acid, 3-hydroxy-3-methylglutaric acid, maleic acid, malic acid, succinic acid, fumaric acid, azelaic acid and their esters with aliphatic alcohols having a maximum of 4 carbon atoms, sulfoacetic acid, 2-sulfopropionic acid, 2-sulfobutyric acid, 2-sulfovalerianic acid and their esters with aliphatic alcohols having a maximum of 4 carbon atoms. Among the higher acids substituted by sulfonic groups can be mentioned 2-sulfolaurinic acid, 2-sulfooleic acid, 2-sulfopalmitic acid, 2-sulfostearic acid and their esters of the aforesaid type, as well as corresponding sulfamides or the sulfamides substituted by lower alkyl groups having a maximum of 4 carbon atoms or by alkylene groups with 4 or 5 carbon atoms, acetic acid, propionic, butyric and valerianic acids substituted in the 2-position by an alkyl, sulfoxide or alkylsulfone group in which the alkyl has a maximum of 4 carbon atoms, cyanacetic acid, 2-cyanpropionic acid, 2-cyanbutyric acid, 2-cyanvalerianic acid, aminoacetic acid, 2-aminopropionic acid, 2-aminobutyric acid, 3-aminobutyric acid, 4-aminobutyric acid, 2-aminovalerianic acid, 4-aminovalerianic acid and their derivatives with one or two alkyls substituted on the amino hydrogen with a maximum of 4 carbon atoms or with an alkylene group with 4 or 5 carbon atoms, or derivatives of these compounds with the amino group acylated with a lower aliphatic acid having 1 to 4 carbon atoms or with one of the aforesaid aromatic, alicyclic or heterocyclic acids, or groups of quaternary ammonium salts of tertiary amino groups derived from alkyls having a maximum of 4 carbon atoms, ethionine, di-methylglycine, 3-diethylaminopropionic acid, carnitine, and cysteic acid.

It is possible to prepare metal or organic base salts of the acyl-di-lysogangliosides according to the present invention having free carboxy functions, these salts also being part of the invention.

Of the other derivatives of the invention which possess a free acid function, such as for example esters or amides, peracylated with dibasic acids, it is possible to prepare the metal or organic base salts. The invention also includes salts formed by acid addition of ganglioside derivatives containing a basic function, for example a free amino function, such as esters with aminoalcohols. Of the metal or organic base salts can be mentioned in particular those which can be used in therapy, such as the salts of alkaline or alkaline earth metals, for example salts of potassium, sodium, ammonium, calcium, magnesium or of the earth metals such as aluminum, but also the salts of organic bases, for example of primary, secondary or tertiary amines which are aliphatic, aromatic or heterocyclic, such as methylamine, ethylamine, propylamine, piperidine, morpholine, ephedrine, furfurylamine, choline, ethylenediamine and aminoethanol.

Acids which can give acid addition salts of the ganglioside derivatives according to the invention include in particular hydracids such as hydrochloric acid and hydrobromic acid, phosphoric acid, sulfuric acid, lower aliphatic acids with a maximum of 7 carbon atoms such as formic, acetic or propionic acids, succinic acid or maleic acid. Acids or bases which cannot be used in therapy, such as picric acid, can be used for the purification of the new ganglioside derivatives and also form part of the invention. Due to the close connection between the new derivatives in their free form and in the form of their salts, the present description of the invention refers to one or the other of these forms without distinction, if not explicitly stated to the contrary, unless the meaning excludes this possibility.

Of special mention among the new acyl-di-lysogangliosides in the invention are those in which each of the two acyl groups is substituted by polar functions and their functional derivatives. Preferred among such derivatives are those in which the two acylamino groups are derived from the same acid substituted by polar groups wherein this acid is chosen from the aforesaid list, and having as the basic ganglioside one chosen from the group formed by $GM_1$, $GM_3$, $GD_{1a}$, $GD_{1b}$ and $GT_{1b}$, their sialic esters derived from ethyl, propyl and isopropyl alcohols, n-butyl, isobutyl, tert-butyl, benzyl, allyl, ethoxycarbonylmethyl and cyclohexyl alcohols, the sialic amides and the amides derived from methylamine, ethylamine, propylamine, di-methylamine, diethylamine, pyrrolidine, piperidine, piperazine, morpholine, thiomorpholine, their peracetylates, perpropionylates, perbutyrylates, permaleinylates, permalonylates, persuccinylates and peracylated analogues of the aforesaid sialic esters and amides. Also to be mentioned are mixtures of N-acyl lysogangliosides containing mainly those derived from the gangliosides $GM_1$, $GD_{1a}$, $GD_{1b}$ and $GT_{1b}$, N-acylated with the acids referred to herein, and functional derivatives analogous to those referred to above for derivatives of the single gangliosides, and especially the following N,N'-diacyl-di-lysogangliosides:

di-dichloroacetyl-di-lyso $GM_1$,
di-monochloroacetyl-di-lyso $GM_1$,
di-(3-chloropivaloyl)-di-lyso $GM_1$,
di-monohydroxyacetyl-di-lyso $GM_1$,
di-trifluoroacetyl-di-lyso $GM_1$,
di-trichloroacetyl-di-lyso $GM_1$,
di-tri-bromoacetyl-di-lyso $GM_1$,
di-monomercaptoacetyl-di-lyso $GM_1$,
di-maleyl-di-lyso $GM_1$,
di-(12-hydroxy-stearoyl)-di-lyso $GM_1$,
di-(2-hydroxybutyroyl)-di-lyso $GM_1$,
di-monofluoroacetyl-di-lyso $GM_1$,
di-di-fluoro-acetyl-di-lyso $GM_1$,
di-(3-aminopropionyl)-di-lyso $GM_1$,
di-cyanoacetyl-di-lyso $GM_1$,
di-(3-di-ethylaminopropionyl)-di-lyso $GM_1$,
di-aminoacetyl-di-lyso $GM_1$, and the esters, amides and peracylates analogous to those mentioned previously.

Of the N -or N'-monoacyl-N,N'-di-lysogangliosides with acyl groups substituted by polar functions can be mentioned those corresponding to the aforesaid specific di-acyl-derivatives, for example N-di-chloroacetyl-di-lyso G $M_1$ or N'-dichloroacetyl-di-lyso $GM_1$ and their functional derivatives analogous to those mentioned previously.

Diacyl derivatives should then be considered, in which one acyl group is one of the aforesaid groups substituted by polar functions and the other is derived from an unsubstituted aliphatic acid, for example one of those mentioned previously. Examples of such semisynthetic ganglioside analogues are the following:

N-dichloroacetyl-N'-acetyl-N,N'-di-lyso $GM_1$,
N-dichloroacetyl-N'-propionyl-N,N'-di-lyso $GM_1$,
N-monochloroacetyl-N'-pivaloyl-N,N'-di-lyso $GM_1$,
N-monohydroxyacetyl-N'-acetyl-N,N'-di-lyso $GM_1$,
N-cyanoacetyl-N'-butyryl-N,N'-di-lyso $GM_1$,
N-monofluoroacetyl-N'-palmitoyl-N,N'-di-lyso $GM_1$,
N-mercaptoacetyl-N'-pivaloyl-N,N'-di-lyso $GM_1$,
N-trichloroacetyl-N'-formyl-N,N'-di-lyso $GM_1$,
N-3-chloropivaloyl-N'-2-propylpentanoyl-N,N'-di-lyso $GM_1$,
N-3-aminopropionyl-N'-oleyl-N,N'-di-lyso $GM_1$,
N-aminoacetyl-N'-tert-butyl-acetyl-N,N'-di-lyso $GM_1$ and other similar N,N'-diacyl-N,N'-di-lysogangliosides derived from permutations of the various acyl groups which are involved in the specific mono- and diacylated compounds and their functional derivatives also mentioned previously.

All of the aforesaid derivatives of the new semi-synthetic ganglioside analogues according to the present invention, such as esters, inner esters, amides and peracylates, can be obtained by the same procedures described in the aforesaid patents for the various corresponding ganglioside derivatives. The invention includes in particular also mixtures of these derivatives, as obtained from mixtures of acyl-lysogangliosides according to the invention, prepared in turn from the aforesaid ganglioside mixtures. To prepare di-acyl derivatives in which the acylamino groups are derived from the same acid, it is preferable, for the sake of simplicity, to acylate the di-lysogangliosides in a single operation by the known procedures. The di-lysogangliosides can be obtained from gangliosides or N-lysogangliosides by alkaline hydrolysis, for example with hydroxides of tetraalkylammonium, potassium hydroxide and others.

To prepare products according to the invention in which the acylamino groups are derived from different acids, it is preferable to use the N- or N'-monoacyl derivatives of di-lysogangliosides. The N-monoacyl-di-lysogangliosides can be obtained by selective acylation of the di-lysogangliosides, since the sphingosine amino group is more reactive than the neuraminic one. Mild acylation therefore of the di-lysogangliosides according to the known methods, for example by the acylation methods used in peptide chemistry, will produce the aforesaid monoacyl derivatives on the sphingosine nitrogen. One then proceeds with acylation on the neuraminic nitrogen in the conventional manner. The acylation procedure to obtain the products according to the invention comprises in this case a two-step acylation reaction.

Monoacyl derivatives on the neuraminic nitrogen can be prepared in various ways. One can, for example, start with di-lysogangliosides and proceed with the intermediate provisional protection of the sphingosine amino group, which can be done for example by hydrophobic interaction with phosphatidylcholine, or by acylation with suitable protective groups, subsequent acylation on the neuraminic nitrogen with a derivative of the acid to be introduced into this position, then deprotection on the sphingosine nitrogen. Lastly, it is possible to acylate the di-lysogangliosides on the two amino groups with one and the same acid and to subject the diacyl compound to the action of enzymes capable of selectively splitting the acylamino group alone on the sphingosine nitrogen, for example with enzymes used to obtain lysogangliosides from gangliosides, for example the enzyme glycosphingolipid-ceramidedeacylase (see Scheme 1).

N-monoacyl-N,N'-di-lysogangliosides can also be obtained however by deacylation on the neuraminic nitrogen of N,N'-diacyl-N,N'-di-lysogangliosides effected by selective chemical hydrolysis, for example with 0.1 molar alcoholic potassium hydroxide.

In the acyl-di-lysogangliosides obtained it is possible, if desired, to functionally convert the carboxy groups of the sialic acids or hydroxyls of such acids, for example to convert them into esters or amides or the hydroxyls in their groups can be esterified with acids (to form peracylates).

The procedure for the preparation of N-acyl-N,N'-di-lysogangliosides, N'-acyl-N,N'-di-lysogangliosides and N,N'-diacyl-N,N'-di-lysogangliosides of the present invention comprises acylating the N,N'-di-lysogangliosides or N-acyl-N,N'-di-lysogangliosides or N'-acyl-N,N'-di-lysogangliosides with the acids corresponding to the aforesaid compounds, or in deacylating the suitable N,N'-diacyl-N,N'-di-lysogangliosides selectively on the sphingosine nitrogen or on the neuraminic nitrogen, or mixtures of these compounds and, if desired, converting them into esters, amides or inner esters or into hydroxy peracylates of the compounds obtained. If desired, the products obtained can be converted into salts.

N-acylation according to the aforesaid procedure can be carried out in the known way, for example by reacting the starting products with an acylating agent, preferably with a functional derivative of the acid, the residue of which is to be introduced into the molecule.

It is thus possible to use as a functional derivative of the acid a halogenide or an anhydride and to acylate preferably in the presence of a tertiary base, such as pyridine or collidine. It is possible to work under anhydrous conditions, at room temperature or higher, or the Schotten-Baumann method can be used to advantage under aqueous conditions in the presence of an inorganic base. In some cases it is also possible to use the esters of the acids as reactive functional derivatives. To acylate, it is also possible to use methods with activated carboxy derivatives, such as are used in peptide chemistry, for example the method used with mixed anhydrides or derivatives obtainable with derivatives of carbodiimides or isoxazole salts.

Of all the various preparation methods, the most suitable are the following:

1. reaction of the lysoganglioside derivative with the azide of the acid;
2. reaction of the lysoganglioside derivative with an acylimidazole of the acid obtainable from the acid with N,N'-carbonyldiimidazole;
3. reaction of the lysoganglioside derivative with a mixed anhydride of the acid and of trifluoro-acetic acid;
4. reaction of the lysoganglioside derivative with the chloride of the acid;
5. reaction of the lysoganglioside derivative with the acid in the presence of a carbodiimide (such as dicyclohexylcarbodiimide) and optionally a substance such as 1-hydroxybenzotriazole;
6. reaction of the lysoganglioside derivative with the acid by heating;
7. reaction of the lysoganglioside derivative with a methyl ester of the acid at a high temperature;
8. reaction of the lysoganglioside derivative with a phenol ester of the acid, for example reaction of an ester with para-nitrophenol;
9. reaction of the lysoganglioside derivative with an ester derived from the exchange between a salt of the acid and 1-methyl-2-chloropyridinium iodide.

It has already been noted how partial, selective acylations can be obtained both on the sphingosine nitrogen and on the neuraminic nitrogen. Scheme 1 illustrates these procedures.

The enzymatic deacylation of N,N'-diacyl-N,N'-di-lysogangliosides on the sphingosine nitrogen as previously reported can be carried out under the conditions used for the partial deacylation of gangliosides, for example as described in J. Biochem., 103, 1 (1988). The double deacylation of N,N'-diacyl-N,N'-di-lysogangliosides to N,N'-di-lysogangliosides can be carried out in the same way as the preparation of de-N-acetyl lysogangliosides as described, for example, in Biochemistry 24, 525 (1985); J. Biol. Chem. 255, 7657, (1980); Biol. Chem. Hoppe Seyler 367, 241, (1986): Carbohydr. Research 179, 393 (1988); Bioch. Bioph. Res. Comn. 147, 127 ( 987).

The aforesaid publication in Carbohydr. Research 179 also contains a description of a method for the selective deacylation on the neuraminic nitrogen obtainable by the action of KOH 0.1M in 90% n-butanol of the ganglioside $GM_3$, deacylation which can be applied to the N,N'-diacyl-N,N'-di-lysogangliosides of the present invention to obtain N-acyl-N,N'-di-lysogangliosides.

Of course, the preparation methods of this type which come within the scope of the present invention include also all the chemical equivalents which would be evident to an expert in the art.

SCHEME 1

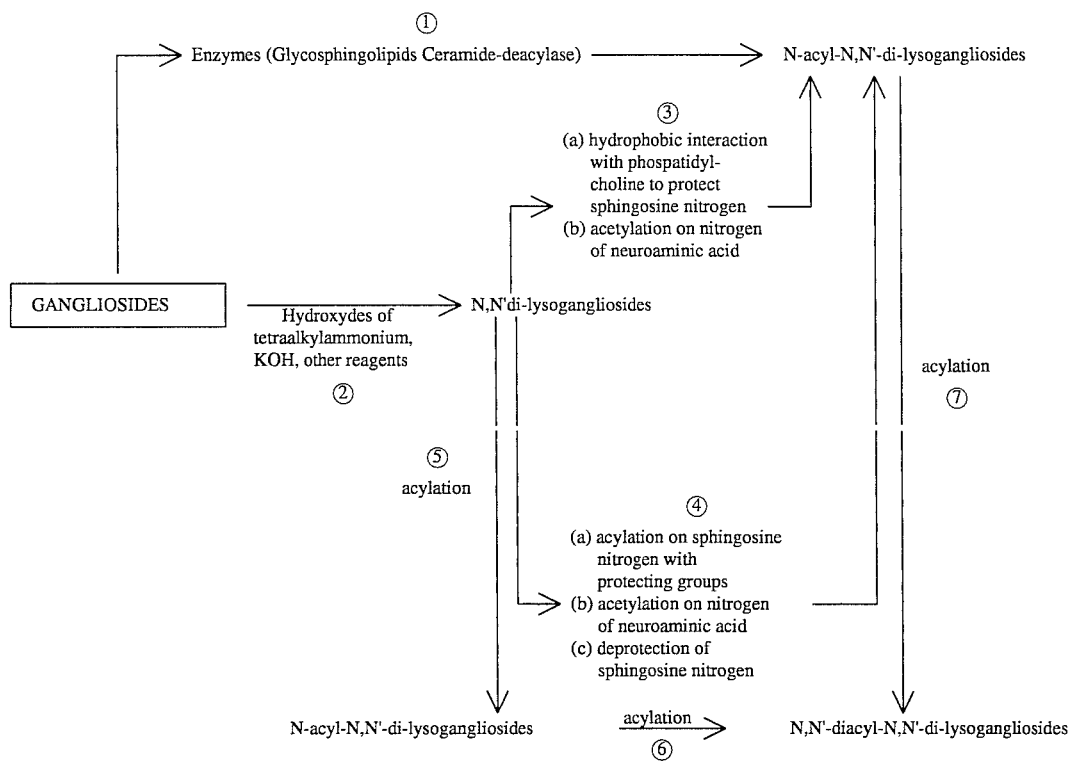

The preparation of carboxy or hydroxy derivatives of the new acyl lysogangliosides obtained according to the aforesaid procedure can be effected by the known procedures, excluding those methods which would have the effect of altering the basic ganglioside structure, such as those which would require the use of highly acidic agents or which would have to be effected under drastically alkaline or acidic conditions, or also those methods which would lead to an undesired alkylation of the hydroxy groups of the saccharide part of the molecule.

Esterification of the carboxy groups of the N-acyl gangliosides or their conversion into amides can be effected for example as described in U.S. Pat. No. 4,713,374 for gangliosides. The formation of inner esters of the new derivatives can also be effected in the same way as the preparation of the inner esters of gangliosides, as described for example in U.S. Pat. No. 4,593,091 and in EP patent No. 0072 722. These inner esters not only include the compounds formed by lactonization of the sialic carboxy groups with saccharide hydroxyls, but also those for example which contain lactone rings formed between the sialic carboxyls and the sialic hydroxyls, the latter being in turn bound to the saccharide part, and also other possible lactone structures. The procedure of the aforesaid patents for the formation of inner esters comprises treating a ganglioside in a non-aqueous organic solvent under anhydrous conditions with a lactonizing agent, The most suitable organic solvents include dimethylsulfoxide, dimethylformamide, sulfolane, tetrahydrofuran, di-methoxyethane, pyridine or mixtures of these solvents. Suitable reagents for the lactonization reaction include carbodiimides soluble in organic solvents, such as dicyclohexylcarbodiimide, benzylisopropylcarbodiimide, benzylethylcarbodiimide, salts of 2-chloro-l-methylpyridine, ethoxyacetylene and Woodward's reagent (N-ethyl-5-phenyl-isoxazole-3'-sulfonate). Older methods use the reaction between a ganglioside and acetic or trichloroacetic acid or with a carbodiimide soluble in water or in an aqueous medium. All of these methods can also be used for the preparation of inner esters of the new N-acyl-lysogangliosides of the invention.

For the "outer" esterification of carboxy groups, that is, esterification with alcohols of the aforesaid series, it is possible for example to react the N-acyl-lysogangliosides with the desired alcohol, in the presence of an ion exchanger, for example a Dowex-50-type resin, the yield being limited due to the simultaneous formation of inner esters and the reaction times being rather long.

Another esterification method comprises passing the alcohol over a resin such as Dowex-50Wx8 (100–200 mesh form H) and treating the dissolved eluate in the same alcohol with the corresponding diazoalkane.

Another suitable preparation method for esters comprises treating a metal salt of the lysoganglioside derivative with an etherifying agent. Salts of alkaline or alkaline-earth metals are used, but any other metal salt can also be used. As etherifying agent it is possible to use those mentioned in the literature, especially the esters of various inorganic acids, or organic sulfonic acids, such as hydracids, that is, in other words, hydrocarbyl halogenides, such as methyl iodide, ethyl iodide, etc., or neutral or acid sulfates of hydrocarbyls, sulfites, carbonates, silicates, phosphites, etc. or hydrocarbyl sulfonates, such as for example methyl benzene or p-toluenesulfonate. Reaction can be carried out in a suitable solvent, for example an alcohol, preferably the one corresponding to the alkyl group to be introduced, but also in nonpolar solvents, such as ketones, ethers such as dioxane or dimethylsulfoxide.

A particularly advantageous method of esterification comprises treating an inner ester of the lysoganglioside derivative with a mixture of the alcohol desired and of its corresponding alcoholate. Reaction can be conducted at a temperature corresponding to the boiling point of the alcohol, however, it is also possible to use lower temperatures, the reaction times in this case being longer.

The amides of the lysoganglioside derivatives of the present invention can be prepared by known methods and especially the following:

a) reaction of the inner esters of the N-acyl lysoganglioside derivatives with ammonia or with amines;

b) reaction of the carboxy esters of the N-acyl lysoganglioside derivatives with ammonia or amines;

c) reaction of the N-acyl lysoganglioside derivatives with activated carboxy groups with ammonia or amines;

Reaction a) can be effected by direct treatment, with or without solvent, of the ganglioside inner ester with ammonia or with the amine of which the amide is to be prepared. Reaction can also be effected at quite low temperatures, such as for example between −5° and +10°, but preferably at room temperature or higher, for example from 30 to 120° C. As solvents it is possible to use ketones, aromatic hydrocarbons, dimethylformamide, dimethylsulfoxide, dioxane or tetrahydrofuran.

Reaction b) also can be effected preferably under the conditions described for a). Apart from the esters described for the present invention it is possible to use other esters, for example esters with phenols. To activate the carboxy group in the reaction mentioned in c) above, methods known in the field of peptide chemistry are used, avoiding those which involve using acidic or basic conditions which would lead to the disintegration of the ganglioside molecule. If the starting gangliosides are in the form, for example, of sodium salts, it is advisable to first treat the salt with an ion exchange resin of the Dowex type or another acid ion exchanger. For example, a condensation method in the presence of carbodiimides is used, for example dicyclohexylcarbodiimide, benzylisopropylcarbodiimide or benzylethylcarbodiimide, in the presence of 1-hydroxybenzotriazol or condensation in the presence of N,N'-carbonyldiimidazol.

Acylation of the hydroxy groups of the saccharide, sialic part and possibly of the ceramide residue in the molecule can also be effected in the known way, for example by acylation with a halogenide or an anhydride of the acid with which one wishes to acylate, preferably in the presence of a tertiary base, such as pyridine or collidine. The aforesaid peracylated derivatives are thus obtained.

It is also possible, according to the definition of the procedure of the present invention, to acylate a de-N-acetyl lysoganglioside and to recover the acetylamino group in neuraminic acid after acylation. This acetylation can also be carried out in the known way; in this case, relatively mild methods of N-acylation are chosen, in order to leave the hydroxy group of the neuraminic acid unaltered. The acetylation of this group, to be carried out after the acylation reaction on the sphingosine nitrogen, can be done by drastic methods, especially by using acetic anhydride.

Lastly, in all the compounds obtainable according to the aforesaid procedures which present salifiable groups, it is possible to salify such groups in the known way in order to obtain desired salts.

The invention also includes modifications of the preparation procedures for the new derivatives, in which a procedure can be interrupted at any one stage or which are begun with an intermediate compound and the remaining stages are carried out, or in which the starting products are formed in situ.

Another object of the present invention is directed to pharmaceutical preparations containing as active substance one or more of the new acyl lysoganglioside derivatives of the invention, and in particular, those which are described herein.

The pharmaceutical preparations can be formulations for oral, rectal, parenteral, local or transdermal use. They are therefore in solid or semisolid form, for example pills, tablets, gelatinous capsules, capsules, suppositories or soft gelatin capsules. For parenteral use it is possible to use those forms intended for intramuscular, subcutaneous or transdermal administration, or those suitable for infusions or intravenous injections and which can therefore be presented as solutions of the active compounds or as freeze-dried powders of the active compounds to be mixed with one or more pharmaceutically acceptable excipients or diluents, suitable for the above uses and compatible with the physiological fluids. For local use, preparations in the form of sprays can be considered, for example nasal sprays, creams or ointments for topical use or specially medicated plasters for transdermal administration.

The preparations of the invention can be administered to human patients or animals. They contain preferably from 0.01% to 10% by weight of active component for solutions, sprays, ointments and creams and from 1% and 100% by weight, preferably from 5% to 50% by weight, of active compound for preparations in solid form. The dosage to be administered depends on individual indications, on the desired effect and on the chosen administration route.

Another object of the present invention is represented by the therapeutic use of both the new acyl-lysogangliosides and those which are already known as substances and which are listed above. This therapeutic use concerns mainly the aforesaid indications. Daily dosages to man by injection (subcutaneous or intramuscular) or by the oral route, vary from 0.05 mg to 5 mg of active substance per kg of body weight.

The following Examples illustrate the preparation of the acyl-lysogangliosides of the present invention, pharmaceutical preparations containing them as active ingredients, and their therapeutic use. These Examples are not to be considered as limiting of the present invention.

EXAMPLE 1

DI-LYSO $GM_1$ 10 gr of $GM_1$ are dissolved in 200 ml KOH 3N and reacted by hydrolysis for 72 hrs at 90° C. The solution is cooled and brought to pH 6.5 with hydrochloric acid. It is left to rest for 18 hrs at 4° C. after which the precipitated fatty acids are filtered away. It is dialyzed against water and concentrated to 500 ml and precipitated in 5 liters (lt) of acetone.

The product is dried and high performance preparative chromatography on silica gel is effected using as eluent a mixture of chloroform/methanol/$NH_3$ 5N (55:45:10).

The fractions containing the product are dried and then redissolved in water. It is brought to pH 10 with NaOH 0.01N and dialyzed, concentrated to 100 mg/ml and precipitated in 5 volumes of acetone. Yield of di-lyso $GM_1$ 5.7 g (70% theoretical).

Chromatography on a silica gel plate with a solvent formed by chloroform/methanol/$NH_3$ 5N (55:45:10) shows the product to be a unitary compound with Rf=0.05 ($GM_1$= 0.35).

EXAMPLE 2

N,N'-DI-DICHLOROACETYL-DI-LYSO $GM_1$ 500 mg (0.39 mM) of $GM_1$ are dissolved in 2.5 ml of dimethylformamide/methanol 1:1 and to this solution are added, at 0° C., 0.55 ml (7.92 mM) of triethylamine and 0.41 ml (3.96 mM) of methyl dichloroacetate. Reaction is conducted at room temperature for 168 hrs. The reaction mixture is precipitated in 20 volumes of ethyl acetate, filtered and dried.

The product is then purified by silica gel chromatography using as eluent a mixture of chloroform/methanol/water (60:25:4).

The pure fractions are pooled, evaporated, gathered with $Na_2CO_3$ 1N, dialyzed against distilled water and then concentrated to 5 ml and precipitated in 50 ml of acetone.

Product obtained: 529 mg (90% theoretical). Chromatography on a silica gel plate with a solvent formed by chloroform/methanol/$CaCl_2$ 0.3% (60:35:8), shows the product to be a unitary compound with Rf=0.52.

EXAMPLE 3

N,N'-DI-(3-DIETHYLAMINOPROPIONYL)-DI-LYSO $GM_1$ 500 mg (0.39 mM) of di-lyso $GM_1$ are dissolved in 2.5 ml of dimethylformamide and to this solution are added at room temperature 1.1 ml (7.92 mM) of triethylamine, 0.72 g (3.96 mM) of 3-diethylaminopropionic acid and 0.4 g (1.50 mM) of chloromethylpyridinium iodide dissolved in 2.5 ml of dimethylformamide. The resulting solution is reacted for 18 hrs at room temperature and then precipitated in 100 ml of acetone. It is filtered and dried. The product is then purified by silica gel chromatography using as eluent a mixture of chloroform/methanol/water (68:35:8).

The pure fractions are pooled, evaporated, gathered with $Na_2CO_3$ 1N, dialyzed against distilled water and then concentrated to 5 ml and precipitated in 50 ml of acetone.

Product obtained: 378 mg (60% theoretical). Chromatography on a silica gel plate using as solvent chloroform/methanol/$NH_3$ 5N 55:45:10 shows the product to be a unitary compound with Rf=0.08.

EXAMPLE 4

N,N'-DI-DIFLUOROACETYL-DI-LYSO $GM_1$ 500 mg (0.39 mM) of di-lyso $GM_1$ are dissolved in 2.5 ml of dimethylformamide and to this solution are added at room temperature 1.1 ml (7.92 mM) of triethylamine, 0.25 ml (3.96 mM) of difluoroacetic acid and 0.4 gr (1.50 mM) of chloromethylpyridinium iodide dissolved in 2.5 ml of dimethylformamide. It is reacted for 18 hrs at room temperature and then precipitated in 100 ml of acetone, filtered and dried.

The product is then purified by silica gel chromatography using as eluent a mixture of chloroform/methanol/water (60:25:4).

The pure fractions are pooled, evaporated, gathered with $Na_2CO_3$ 1N, dialyzed against distilled water and then concentrated to 5 ml and precipitated in 50 ml of acetone.

Product obtained: 393 mg (70% theoretical). Chromatography on a silica gel plate with a solvent formed by chloroform/methanol/$CaCl_2$ 0.3% 60:35:8 shows the product to be a unitary compound with Rf=0.30.

EXAMPLE 5

N,N'-DI-MONOFLUOROACETYL-DI-LYSO $GM_1$ 500 mg (0.39 mM) of di-lyso $GM_1$ are dissolved in 2.5 ml of dimethylformamide and to this solution are added at room temperature 1.1 ml (7.92 mM) of triethylamine, 0.39 gr (3.96 mM) of sodium fluoroacetate and 0.4 gr (1.50 mM) of chloromethylpyridinium iodide dissolved in 2.5 ml of dimethylformamide.

It is reacted for 18 hrs at room temperature and then precipitated in 100 ml of acetone, filtered and dried.

The product is then purified by silica gel chromatography using as eluent a mixture of chloroform/methanol/water 60:25:4.

The pure fractions are pooled, evaporated, gathered with $Na_2CO_3$ 1N, dialyzed against distilled water and then concentrated to 5 ml and precipitated in 50 ml of acetone.

Product obtained: 410 mg (75% theoretical). Chromatography on a silica gel plate with a solvent formed by chloroform/methanol/$CaCl_2$ 2 0.3% 60:35:8 shows the product to be a unitary compound with Rf=0.24.

EXAMPLE 6

N,N'-DI-MALEYL-DI-LYSO $GM_1$ 500 mg (0.39 mM) of di-lyso $GM_1$ are dissolved in 2.5 ml of dimethylformamide and to this solution are added 1.1 ml (7.92 mM) of triethylamine and 0.77 gr (7.92 mM) of maleic anhydride. The mixture is reacted for 72 hrs at room temperature, precipitated in 20 volumes of ethyl acetate, filtered and dried.

The product is then purified by silica gel chromatography using as eluent a mixture of chloroform/methanol/water 60:35:8.

The pure fractions are pooled, evaporated, gathered with $Na_2CO_3$ 1N, dialyzed against distilled water and then concentrated to 5 ml and precipitated in 25 ml of acetone.

Product obtained: 494 mg (83% theoretical). Chromatography on a silica gel plate with a solvent formed by butanol/methanol/water 1.1:1.1:0.5 shows the product to be a unitary compound with Rf=0.12.

EXAMPLE 7

N,N'-DI-MONOMETHOXYACETYL-DI-LYSO $GM_1$ 500 mg (0.39 mM) of di-lyso $GM_1$ are dissolved in 2.5 ml of dimethylformamide and to this solution are added at room temperature 1.1 ml (7.92 mM) of triethylamine, 0.3 ml (3.96 mM) of methoxyacetic acid and 0.4 gr (1.50 mM) of chloromethylpyridinium iodide dissolved in 2.5 ml of dimethylformamide.

The mixture is reacted for 18 hrs at room temperature and then precipitated in 100 ml of acetone, filtered and dried.

The product is then purified by silica gel chromatography using as eluent a mixture of chloroform/ methanol/water 60:25:4.

The pure fractions are pooled, evaporated, gathered with $Na_2CO_3$ 1N, dialyzed against distilled water and then concentrated to 5 ml and precipitated in 50 ml of acetone.

Product obtained: 278 mg (70% theoretical). Chromatography on a silica gel plate with a solvent formed by chloroform/methanol/$CaCl_2$ $_{0.3}$% 60:35:8 shows the product to be a unitary compound with Rf=0.33.

EXAMPLE 8

N,N'-DI-TRICHLOROACETYL-DI-LYSO $GM_1$ 500 mg (0.39 mM) of di-lyso $GM_1$ are dissolved in 2.5 ml of dimethylformamide/methanol 1:1 and to this solution are added, at 0° C., 1.1 ml (7.92 mM) of triethylamine and 0.47 ml (3.96 mM) of methyl trichloroacetate and it is reacted at room temperature for 168 hrs. It is precipitated in 20 volumes of ethyl acetate, filtered and dried.

The product is then purified by silica gel chromatography using as eluent a mixture of chloroform/methanol/water 60:25:4.

The pure fractions are pooled, evaporated, gathered with $Na_2CO_3$ 1N, dialyzed against distilled water and then concentrated to 5 ml and precipitated in 50 ml of acetone.

Product obtained: 400 mg (65% theoretical). Chromatography on a silica gel plate with a solvent formed by chloroform/methanol/$CaCl_2$ 0.3% 60:35:8 shows the product to be a unitary compound with Rf=0.37.

EXAMPLE 9

N,N'-DI-TRIFLUOROACETYL-DI-LYSO $GM_1$ 500 mg (0.39 mM) of di-lyso $GM_1$ are dissolved in 2.5 ml of dimethylformamide/methanol 1:1 and to this are added, at 0° C., 1.1 ml (7.92 mM) of triethylamine and 0.40 ml (3.96 mM) of methyl trifluoroacetate, and it is reacted at room temperature for 168 hrs. It is precipitated in 20 volumes of ethyl acetate, filtered and dried.

The product is then purified by silica gel chromatography using as eluent a mixture formed by chloroform/methanol/water 60:25:4.

The pure fractions are pooled, evaporated, gathered with $Na_2CO_3$ 1N, dialyzed against distilled water and then concentrated to 5 ml and precipitated in 50 ml of acetone.

Product obtained: 300 mg (52% theoretical). Chromatography on a silica gel plate with a solvent formed by chloroform/methanol/$CaCl_2$ 2 0.3% 60:35:8 shows the product to be a unitary compound with Rf=0.38.

EXAMPLE 10

N,N'-DI-MONOHYDROXYACETYL-DI-LYSO $GM_1$ 500 mg (0.39 mM) of di-lyso $GM_1$ are dissolved in 2.5 ml of dimethylformamide and to this are added, at 0° C., 1.1 ml (7.92 mM) of triethylamine and glycolic anhydride, freshly prepared by reacting 3 gr (39.6 mM) of glycolic acid and 1.6 gr (7.92 mM) of dicyclohexylcarbodiimide dissolved in 20 ml of tetrahydrofuran, and filtering away, 2 hrs later, the dicyclohexylurea which has formed.

The condensation reaction is carried out at 0° C. for 18 hrs under stirring. At the end of the reaction the solution is concentrated to 1 ml, and then precipitated in 10 ml of acetone and vacuum dried.

The product is then purified by silica gel chromatography using as eluent a mixture of chloroform/methanol/water 60:25:4.

The pure fractions are pooled, evaporated, gathered with $Na_2CO_3$ 1N, dialyzed against distilled water and then concentrated to 5 ml and precipitated in 50 ml of acetone.

Product obtained: 495 mg (96% theoretical). Chromatography on a silica gel plate with a solvent formed by chloroform/methanol/$CaCl_2$ 2 0.3% 60:35:8 shows the product to be a unitary compound with Rf=0.28.

EXAMPLE 11

N,N'-DI-(3-CHLOROPIVALOYL)-DI-LYSO $GM_1$ 500 mg (0.39 mM) of di-lyso $GM_1$ are dissolved in 2.5 ml of dimethylformamide and to this solution are added at room temperature 1.1 ml (7.92 mM) of triethylamine, 0.54 gr (3.96 mM) of beta-chloro pivalic acid and 0.4 gr (1.50 mM) of chloromethylpyridinium iodide dissolved in 2.5 ml of dimethylformamide. The mixture reacted for 18 hrs at room temperature and then precipitated in 100 ml of acetone. It is filtered and dried.

The product is then purified by silica gel plate chromatography using as eluent a mixture of chloroform/methanol/water 60:25:4.

The pure fractions are pooled, evaporated, gathered with $Na_2CO_3$ 1N, dialyzed against distilled water and then concentrated to 5 ml and precipitated in 50 ml of acetone.

Product obtained: 404 mg (68% theoretical).

Chromatography on a silica gel plate with a solvent formed by chloroform/methanol/$CaCl_2$ 2 0.3% 60:35:8 shows the product to be a unitary compound with Rf=0.41.

EXAMPLE 12

N,N'-DI-MONOCHLOROACETYL-DI-LYSO $GM_1$ 500 mg (0.39 mM) of di-lyso $GM_1$ are dissolved in 2.5 ml of dimethylformamide/methanol 1:1 and to this solution are added, at 0° C., 1.1 ml (7.92 mM) of triethylamine and 0.67 gr (3.96 mM) of chloroacetic anhydride. The mixture is reacted for 168 hrs at room temperature. It is precipitated in 20 volumes of ethyl acetate, filtered and dried.

The product is then purified by silica gel chromatography using as eluent a mixture of chloroform/methanol/water 60:25:4.

The pure fractions are pooled, evaporated, gathered with $Na_2CO_3$ 1N, dialyzed against distilled water and then concentrated to 5 ml and precipitated in 50 ml of acetone.

Product obtained: 479 mg (80% theoretical). Chromatography on a silica gel plate with a solvent formed by chloroform/methanol/$CaCl_2$ 2 0.3% 60:35:8 shows the product to be a unitary compound with Rf=0.38.

EXAMPLE 13

N-DICHLOROACETYL-N'-BUTYRYL-DI-LYSO $GM_1$ 500 mg of di-lyso $GM_1$ (0.39mM) are dissolved in 5 ml of dimethylformamide, and to this solution are slowly added 145 mg (0.43 mM) of 9-fluorenyl-methyloxycarbonyl-N-hydroxysuccinimide (FMOC-succ.) and it is left to react for 1 hr at room temperature. At the end of the reaction it is precipitated in 100 ml of acetone, filtered and dried. The product is then purified by silica gel chromatography using as elution solvent a mixture of chloroform/methanol/water 60:30:6.

The fractions containing the intermediate reaction product (N-FMOC-di-lyso $GM_1$) are pooled, dried and then redissolved in 2.5 ml of dimethylformamide/methanol 1:1 and to this solution are added, at 0° C., 1.1 ml (7.92 mM) of triethylamine and 626 mg (3.96 mM) of butyric anhydride. The resulting mixture is reacted at room temperature for 2 hrs. Then, 1 ml of piperidine is added to the reaction mixture to remove the fluorenyl group. It is left to react for 18 hrs at room temperature and then precipitated in 100 ml of acetone/water 9:1, filtered and dried.

The intermediate reaction product is dissolved in 30 ml of chloroform/methanol/water 1:1:0.1 and to this solution are added 1.1 ml (7.92 mM) of triethylamine and 0.41 ml (3.96 mM) of methyl dichloroacetate. It is left to react for 2 hrs at room temperature, dried, redissolved with 5 ml of $Na_2CO_3$ 1M and kept at a temperature of 60° C. for 1 hr. It is dialyzed, concentrated to 5 ml and precipitated in 5 volumes of acetone.

The reaction product is purified by silica gel chromatography using as elution solvent a mixture of chloroform/methanol/$NH_3$ 2.5N 60:35:8.

The pure fractions are pooled, evaporated, redissolved in 2.0 ml of chloroform/methanol 1:1 and precipitated in 10 ml of acetone.

Product obtained =282 mg (54% theoretical). Chromatography on a silica gel plate with a solvent formed by chloroform/methanol/$CaCl_2$ 2 0.3% 50:42:11, shows the product to be a unitary compound with Rf=0.36.

EXAMPLE 14

N-DICHLOROACETYL-N'-METHOXYACETYL-DI-LYSO $GM_1$ 500 mg of di-lyso $GM_1$ (0.39mM) are dissolved in 5 ml of dimethylformamide, and to this solution are slowly added 145 mg (0.43 mM) of 9-fluorenyl-methyloxycarbonyl-N-hydroxysuccinimide (FMOC-succ.). The mixture is left to react for 1 hr at room temperature.

At the end of the reaction it is precipitated in 100 ml of acetone, filtered and dried. The product is then purified by silica gel chromatography using as elution solvent a mixture of chloroform/methanol/water 60:30:6.

The fractions containing the intermediate reaction product (N-FMOC-di-lyso $GM_1$) are pooled, dried and then redissolved in 2.5 ml of dimethylformamide/methanol 1:1 and to this solution are added, at 0° C., 1.1 ml (7.92 mM) of triethylamine, 0.3 ml (3.96 mM) of methoxyacetic acid and 0.4 gr (1.50 mM) of chloromethylpyridinium iodide dissolved in 2.5 ml of DMF. It is reacted at room temperature for 18 hrs.

To the reaction mixture is then added 1 ml of piperidine to remove the fluorenyl group. It is left to react for 18 hrs at room temperature and then precipitated in 100 ml of acetone/water 9:1, filtered and dried.

The intermediate reaction product is dissolved in 30 ml of chloroform/methanol/water 1:1:0.1 and to this are added 1.1 ml (7.92 mM) of triethylamine and 950 mg (3.96 mM) of dichloroacetic anhydride. This mixture is left to react for 2 hrs at room temperature, dried, redissolved with 5 ml of $Na_2CO_3$ 1M and kept at a temperature of 60° C. for 1 hr. It is dialyzed, concentrated to 5 ml and precipitated in 5 volumes of acetone.

The reaction product is purified by silica gel chromatography using as elution solvent a mixture of chloroform/methanol/$NH_3$ 2.5N 60:35:8.

The pure fractions are pooled, evaporated, redissolved in 2.0 ml of chloroform/methanol 1:1 and precipitated in 10 ml of acetone.

Product obtained =259 mg (46% theoretical). Chromatography on a silica gel plate with a solvent formed by chloroform/methanol/$CaCl_2$ 0.3% 50:42:11, shows the product to be a unitary compound with Rf=0.38.

EXAMPLE 15

N-ACETYL-N'-DICHLOROACETYL-DI-LYSO $GM_1$ 500 mg of di-lyso $GM_1$ (0.39mM) are dissolved in 5 ml of dimethylformamide, and to this solution are slowly added 145 mg (0.43 mM) of 9-fluorenyl-methyloxycarbonyl-N-hydroxysuccinimide (FMOC-succ.). It is left to react for 1 hr at room temperature.

At the end of the reaction it is precipitated in 100 ml of acetone, filtered and dried. The product is then purified by silica gel chromatography using as elution solvent a mixture of chloroform/methanol/water 60:30:6.

The fractions containing the intermediate reaction product (N-FMOC-di-lyso $GM_1$) are pooled, dried and then redissolved in 2.5 ml of dimethylformamide/methanol 1:1 and to this solution are added, at 0° C., 1.1 ml (7.92 mM) of triethylamine and 950 mg (3.96 mM) of dichloroacetic anhydride, which is then reacted at room temperature for 2 hrs.

To the reaction mixture is then added 1 ml of piperidine to remove the fluorenyl group. The mixture is then left to react for 18 hrs at room temperature and precipitated in 100 ml of acetone/water 9:1, filtered and dried. The intermediate reaction product is dissolved in 30 ml of chloroform/methanol/water 1:1:0.1 and to this solution are added 1.1 ml (7.92 mM) of triethylamine and 373 µl (3.96 mM) of acetic anhydride. It is left to react for 2 hrs at room temperature, dried, redissolved with 5 ml of $Na_2CO_3$ 1M and kept at a temperature of 60° C. for 1 hr. It is dialyzed, concentrated to 5 ml and precipitated in 5 volumes of acetone.

The reaction product is purified by silica gel chromatography using as elution solvent a mixture of chloroform/methanol/$NH_3$ 2.5N 60:35:8.

The pure fractions are pooled, evaporated, redissolved in 2.0 ml of chloroform/methanol 1:1 and precipitated in 10 ml of acetone.

Product obtained =266 mg (53% theoretical). Chromatography on a silica gel plate with a solvent formed by chloroform/methanol/$CaCl_2$ 2 0.3% 50:42:11, shows the product to be a unitary compound with Rf=0.34.

EXAMPLE 16

N'-DICHLOROACETYL-DI-LYSO $GM_1$ 500 mg of di-lyso $GM_1$ (0.39mM) are dissolved in 5 ml of dimethylformamide, and to this solution are slowly added 145 mg (0.43 mM) of 9-fluorenyl-methyloxycarbonyl-N-hydroxysuccinimide dissolved in 2 ml of tetrahydrofuran. It is left to react for 1 hr at room temperature.

At the end of the reaction 467.7 mg (1.95 mM) of di-chloroacetic anhydride and 54.5 µl (0.39 mM) of triethylamine are added.

30 minutes later, 2 ml of piperidine are added to remove the protector group. It is left to react for 18 hrs at room temperature and precipitated in 100 ml of acetone. It is filtered and dried. The product thus obtained is dissolved in 10 ml of $Na_2CO_3$ 1M and kept at a temperature of 60° C. for 1 hr. It is dialyzed, concentrated to 5 ml and precipitated in 5 volumes of acetone.

The reaction product is purified by silica gel chromatography using as elution solvent a mixture of chloroform/methanol/$NH_3$ 2.5N 60:35:8. The fractions containing the pure product are dried and then redissolved in 5 ml of water.

It is brought to pH 10 with NaOH 0.01N and dialyzed, concentrated to 5 ml and precipitated in 50 ml of acetone.

Product obtained =315 mg (59% theoretical). Chromatography on a silica gel plate with a solvent formed by chloroform/methanol/CaCl$_2$ 2 0.3% 50:42:11, shows the product to be a unitary compound with Rf=0.30 and positive to ninhydrin staining.

EXAMPLE 17

N-DICHLOROACETYL-DI-LYSO GM$_1$ 500 mg of di-lyso GM$_1$ (0.39mM) are dissolved in 5 ml of dimethylformamide, and to this solution are slowly added 145 mg (0.43 mM) of 9-fluorenyl-methyloxycarbonyl-N-hydroxysuccinimide (FMOC-succ.), and it is left to react for 1 hr at room temperature. At the end of the reaction it is precipitated in 100 ml of acetone, filtered and dried. The product is then purified by silica gel chromatography using as elution solvent a mixture of chloroform/methanol/water 60:30:6.

The fractions containing the intermediate reaction product N-FMOC-di-lyso GM$_1$ are pooled, dried and then redissolved in 2.5 ml of dimethylformamide/methanol 1:1 and to this solution are added, at 0° C., 1.1 ml (7.92 mM) of triethylamine and 0.40 ml (3.96 mM) of methyl trifluoroacetate. It is reacted at room temperature for 3 days.

To this reaction mixture is then added 1 ml of piperidine to remove the fluorenyl group. It is left to react for 18 hrs at room temperature and precipitated in 100 ml of acetone/water 9:1, filtered and dried.

The intermediate reaction product is dissolved in 30 ml of chloroform/methanol/water 1:1:0.1 and to this solution are added 545 µl (3.96 mM) of triethylamine and 400 µl (3.96 mM) of methyl dichloroacetate. It is left to react for 2 hrs at room temperature, dried, redissolved with 5 ml of water and brought to pH 9.0 with NaOH 0.01N. The mixture is again left to react at room temperature for 2 hrs to remove the trifluoroacetyl group. It is dialyzed, concentrated to 3 ml and precipitated in 15 ml of acetone.

The raw product obtained is purified by silica gel chromatography using as eluent a mixture of chloroform/methanol/water 60:35:8.

The pure fractions are pooled, evaporated, redissolved in 2 ml of chloroform/methanol 1:1 and precipitated in 10 ml of acetone.

Product obtained =251.4 mg (47% theoretical). Chromatography on a silica gel plate with a solvent formed by chloroform/methanol/CaCl$_2$ 2 0.3% 50:42:11, shows the product to be a unitary compound with Rf=0.15 and positive to ninhydrin staining.

EXAMPLE 18

METHYL ESTER OF N,N'-DI-DICHLOROACETYL-DI-LYSO GM$_1$ 500 mg (0.34mM) of N,N'-di-dichloroacetyl-di-lyso GM$_1$ sodium salt are dissolved in 5 ml of N-methylpyrrolidone and to this solution are added 42.0 µl (0.68 mM) of methyl iodide. It is left to react for 3 hrs at room temperature, precipitated in ethyl acetate, filtered and vacuum dried.

The product is then purified by silica gel chromatography using as eluent a mixture of chloroform/methanol/water 60:30:6.

The pure fractions are pooled, evaporated, redissolved in 2.5 ml of chloroform/methanol 1:1 and precipitated in 25 ml of acetone.

Product obtained =457 mg (91% theoretical). Chromatography on a silica gel plate with a solvent formed by chloroform/methanol/CaCl$_2$ 2 0.3% 60:35:8, shows the product to be a unitary compound with Rf=0.58.

EXAMPLE 19

2-BUTYLAMIDE OF N,N'-DI-DICHLOROACETYL-DI-LYSO GM$_1$ 500 mg (0.34mM) of the methyl ester of N,N'-di-dichloroacetyl-di-lyso GM$_1$ are dissolved in 5 ml of pyridine. To this solution are added 2.5 ml of 2-butylamine and it is reacted for 72 hrs at room temperature. At the end of the reaction it is dried, redissolved with 5 ml of chloroform/methanol 1:1 and precipitated in 25 ml of acetone, filtered and vacuum dried.

The product is then purified by silica gel chromatography using as eluent a mixture of chloroform/methanol/water 60:25:4.

The pure fractions are pooled, evaporated, redissolved in 2.5 ml of chloroform/methanol 1:1 and precipitated in 25 ml of acetone.

Product obtained =360 mg (70% theoretical). Chromatography on a silica gel plate with a solvent formed by chloroform/methanol/CaCl$_2$ 0.3% 60:35:8, shows the product to be a unitary compound with Rf=0.69.

EXAMPLE 20

PERACETYLATE OF THE METHYL ESTER OF N,N'-DI-DICHLOROACETYL-DI-LYSO GM$_1$ 500 mg (0.34mM) of the methyl ester of N,N'-di-dichloroacetyl-di-lyso GM$_1$ are dissolved in 5 ml of pyridine. To this solution are added 2.5 ml of freshly distilled acetic anhydride and the mixture is stirred for 72 hrs at room temperature. At the end of the reaction the solution is rotary-evaporated and the residue divided between 10 ml of iced water and 10 ml of ethylacetate; the ethyl acetate is washed with cold HCl 1M, with water and with a NaHCO$_3$ 1M solution. The organic layers are anhydrified with sodium sulfate, evaporated and the residue purified by silica gel chromatography, using a mixture of dichloromethane/ethyl acetate/isopropanol 70:30:45.

The pure fractions are pooled, evaporated, redissolved in 5 ml of ethyl ether and precipitated in 25 ml of n-hexane.

Product obtained =453 mg (62% theoretical). Chromatography on a silica gel plate with a solvent formed by chloroform/methanol/ethyl acetate 70:10:30, and ethyl/isopropanol acetate 95:5, shows the product to be a unitary compound with Rf=0.45 and 0.26 respectively.

EXAMPLE 21

INNER ESTER OF N,N'-DI-DICHLOROACETYL-DI-LYSO GM$_1$ 500 mg (0.34mM) of N,N'-di-dichloroacetyl-di-lyso GM$_1$ sodium salt are dissolved in 5 ml of N-methylpyrrolidone at 4° C. and left to react with 55 µl (0.4 mM) of triethylamine and 100 mg (0.41 mM) of chloromethylpyridinium iodide. The reaction is conducted for 4 hrs with a quantitative yield. The product is precipitated adding 50 ml of acetone, filtered, gathered with 5 ml of chloroform/isopropyl alcohol 1:1 and reprecipitated in 25 ml of acetone.

Product obtained: 480 mg (98% theoretical).

Chromatography on a silica gel plate with a solvent formed by chloroform/methanol/$CaCl_2$ 0.3% 60:35:8, shows the product to be a unitary compound with Rf=0.62.

EXAMPLE 22

PREPARATION OF A GANGLIOSIDE MIXTURE (GA) BY EXTRACTION FROM BOVINE BRAIN TISSUE

Bovine brain cortex is removed from the animal and homogenized in phosphate buffer at pH 6.8. To this material are then added 6 volumes of tetrahydrofuran and the resulting mixture is centrifuged. The supernatant is re-extracted twice with tetrahydrofuran. After centrifugation the nonpolar materials are removed by partitioning with ethyl ether and the aqueous-tetrahydrofuran phase is introduced into an ion exchange column equilibrated with ethanol 50%. To the product from the column is added barium hydroxide and four volumes of iced ethanol. After 18 hrs of refrigeration a precipitate is gathered which is then slightly acidified with hydrochloric acid after being dissolved in water. The solution thus obtained is dialyzed and freeze-dried. The yield at this stage is approximately 0.6 mg of raw ganglioside mixture per gram of nervous tissue used. The freeze-dried powder is dispersed in 20 volumes of chloroform-methanol 2:1. The solution obtained is filtered until it is perfectly clear, after which it is partitioned by adding 0.2 volume of 0.88% potassium chloride solution in water.

The upper layer is separated, dialyzed and freeze-dried. The final yield is approximately 0.3 mg of purified mixture of ganglioside salts per gram of brain tissue.

The ganglioside mixture obtained can be fractioned into various portions representing substantially pure gangliosides (in the sense used in the general description above), using columns of silicic acid and eluting with mixtures of methanol-chloroform. On the average this produces a composition of approximately 40% of ganglioside $GD_{1a}$, 21% of ganglioside $GM_1$, 19% of ganglioside $GT_{1b}$ and 16% of ganglioside $GD_{1b}$.

EXAMPLE 23

PREPARATION OF N-DICHLOROACETYL DERIVATIVES OF A MIXTURE OF N-LYSOGANGLIOSIDES 10 gr (5.3 mM) of a ganglioside mixture (obtained according to example 22) are dissolved in 200 ml of a 0.75M solution of KOH in n-propyl alcohol. Hydrolysis reaction is conducted at 93° C. for 24 hrs. At the end of the reaction it is neutralized with acetic acid, precipitated in 2 liters of acetone and dried. The product thus obtained is then dialyzed at a constant volume (100 ml), partitioned with 5 volumes of chloroform/methanol 2:1 and reprecipitated in acetone.

The intermediate reaction product is redissolved in 100 ml of dimethylformamide and to this solution are slowly added 2.15 gr (6.37 mM) of 9-fluorenylmethyloxycarbonyl-N-hydrosuccinimide dissolved in 20 ml of tetrahydrofuran. It is left to react for 1 hr at room temperature.

At the end of the reaction 3 ml (31.85 mM) of acetic anhydride and 0.9 ml (63.7 mM) of triethylamine are added.

After 30 minutes are added 12.5 ml of piperidine to remove the protector group. The mixture is left to react for 18 hrs at room temperature and precipitated in 2 lt of acetone and dried. The material thus obtained is dissolved in 1M of $Na_2CO_3$ and kept at a temperature of 60° C. for 1 hr. It is dialyzed, concentrated to 100 mg/ml and precipitated in 5 volumes of acetone.

The product, constituted by N-lysogangliosides (>98%) and by N,N'-di-lysogangliosides, is passed through an S-Sepharose column (form $H^+$) equilibrated in methanol. The N-lysogangliosides are then eluted with $NH_4Cl$ 10 mM in methanol.

The fractions containing the product are dried and then redissolved in water. The resulting solution is brought to pH 10 with NaOH 0.01N and dialyzed, concentrated to 100 mg/ml and precipitated in 5 volumes of acetone.

Product obtained =approx. 7.7 gr (90% theoretical). 5 gr (3.1 mM) of N-lysogangliosides are dissolved in 250 ml of chloroform/methanol 1:1 and to this solution are added 3.2 ml (31 mM) of methyl dichloroacetate. It is left to react for 3 days at room temperature, dried, redissolved with 50 ml of chloroform/methanol 1:1 and precipitated in 500 ml of acetone.

Product obtained =approx. 5.1 gr (95% theoretical).

EXAMPLE 24

PHARMACEUTICAL PREPARATIONS IN INJECTABLE SOLUTIONS

Preparation No. 1—one 2 ml vial contains:

| | |
|---|---|
| active substance | mg 5 |
| sodium chloride | mg 16 |
| citrate buffer pH 6 in | ml 2 |
| distilled water to vol. | |

The active substance is chosen from the group formed by the ganglioside derivatives described in any one of Examples 2, 4 and 17.

Preparation No. 2—one 2 ml vial contains:

| | |
|---|---|
| active substance | mg 50 |
| sodium chloride | mg 16 |
| citrate buffer pH 6 in | ml 2 |
| distilled water to vol. | |

The active substance is chosen from the group formed by the ganglioside derivatives described in any one of Examples 5, 6 and 7.

Preparation No. 3—one 4 ml flacon contains:

| | |
|---|---|
| active substance | mg 100 |
| sodium chloride | mg 32 |
| citrate buffer pH 6 in | ml 4 |
| distilled water to vol. | |

The active substance is chosen from the group formed by the ganglioside derivatives described in either one of Examples 10 and 11.

Preparations Nos. 1, 2 and 3 can be directly administered to animals or humans by one of the aforesaid routes. Moreover, the compounds can contain other pharmaceutically active substances.

EXAMPLE 25

PHARMACEUTICAL COMPOSITIONS PREPARED IN TWIN FLACONS

The preparations illustrated in this Example are prepared in twin flacons. The first flacon contains the active substance in the form of a freeze-dried powder in a quantity which can vary between 10% and 90% in weight together with a pharmaceutically acceptable excipient, with glycin or mannitol. The second flacon contains the solvent, as a solution of sodium chloride and a citrate buffer.

The contents of the two flacons should be mixed immediately before administration, when the powdered, freeze-dried active substance dissolves rapidly, forming an injectable solution. The pharmaceutical form consisting of a flacon containing the freeze-dried active substance in powder form, is the preferred form of the present invention.

System No. 1 a. one freeze-dried 2 ml flacon contains:

| active substance | mg 5 |
|---|---|
| glycine | mg 30 | b. one 2 ml vial of solvent contains:

| sodium chloride | mg 16 |
|---|---|
| citrate buffer in distilled water to vol. | ml 2 |

The active substance is chosen from the group formed by the ganglioside derivatives described in Example 18.

System No. 2 a. one 3 ml vial of freeze-dried substance contains:

| active substance | mg 5 |
|---|---|
| mannitol | mg 40 | b. one 2 ml vial of solvent contains:

| sodium chloride | mg 16 |
|---|---|
| citrate buffer in distilled water to vol. | ml 2 |

The active substance is chosen from the group formed by the ganglioside derivatives described in either one of Examples 18 and 21.

System No. 3 a. one 3 ml vial of freeze-dried substance contains:

| active substance | mg 50 |
|---|---|
| glycine | mg 25 | b. one 3 ml vial of solvent contains:

| sodium chloride | mg 24 |
|---|---|
| citrate buffer in distilled water to vol. | ml 3 |

The active substance is chosen from the group formed by the ganglioside derivatives described in Examples 18 and 21.

System No. 4 a. one 3 ml vial of freeze-dried substance contains:

| active substance | mg 50 |
|---|---|
| mannitol | mg 20 | b. one 3 ml vial of solvent contains:

| sodium chloride | mg 24 |
|---|---|
| citrate buffer in distilled water to vol. | ml 3 |

The active substance is chosen from the group formed by the ganglioside derivatives described in Examples 18 and 21.

System No. 5 a. one 5 ml flacon of freeze-dried substance contains:

| active substance | mg 150 |
|---|---|
| glycine | mg 50 | b. one 4 ml vial of solvent contains:

| sodium chloride | mg 32 |
|---|---|
| citrate buffer in distilled water to | ml 4 |

The active substance is chosen from the group formed by the ganglioside derivatives described in Example 20.

System No. 6 a. one 5 ml flacon of freeze-dried substance contains:

| active substance | mg 100 |
|---|---|
| mannitol | mg 40 | b. one 4 ml vial of solvent contains:

| sodium chloride | mg 32 |
|---|---|
| citrate buffer in distilled water to | ml 4 |

The active substance is chosen from the group formed by the ganglioside derivatives described in Example 20.

System No. 7 a. one 3 ml flacon contains:

| micronized, sterile active substance | mg 40 |
|---|---| b. one 3 ml vial of solvent contains:

| Tween 80 | mg 10 |
|---|---|
| sodium chloride | mg 24 |
| phosphate buffer in distilled water to | ml 3 |

The active substance is chosen from the group formed by the ganglioside derivatives described in Example 19.

System No. 8 a. one 5 ml flacon contains:

| micronized, sterile active substance | mg 100 |
|---|---| b. one 4 ml vial of solvent contains:

| Tween 80 | mg | 15 |
|---|---|---|
| soybean lecithin | mg | 5 |
| sodium chloride | mg | 36 |
| citrate buffer in distilled water to | ml | 4 |

The active substance is chosen from the group formed by the ganglioside derivatives described in Example 19.

EXAMPLE 26

PHARMACEUTICAL PREPARATIONS FOR TRANSDERMAL ADMINISTRATION

Preparation No. 1—one plaster contains:

| active substance | mg | 100 |
|---|---|---|
| glycerin | gr | 1.6 |
| polyvinyl alcohol | mg | 200 |
| polyvinyl pyrrolidone | mg | 100 |
| excipient to aid transdermal penetration | mg | 20 |
| water | gr | 1.5 |

The active substance is chosen from the group formed by the ganglioside derivatives described in either one of Examples 18 and 21.

Preparation No. 2—100 gr of ointment contain:

| active substance (in 5 gr of mixed phospholipid liposomes) | gr | 4.0 |
|---|---|---|
| polyethylene glycol monostearate | gr | 1.5 |
| glycerin | gr | 1.5 |
| ester of p-hydroxybenzoic acid | mg | 125 |
| water | gr | 72.9 |

The active substance is chosen from the group formed by the ganglioside derivatives described in either one of Examples 18 and 21.

EXAMPLE 27

PHARMACEUTICAL PREPARATIONS FOR ORAL ADMINISTRATION

Preparation No. 1—one tablet contains:

| active substance | mg | 20 |
|---|---|---|
| microcrystalline cellulose | mg | 150 |
| lactose | mg | 20 |
| amide | mg | 10 |
| magnesium stearate | mg | 5 |

The active substance is chosen from the group formed by the ganglioside derivatives described in any one of Examples 2, 3 and 15.

Preparation No. 2—one tablet contains:

| active substance | mg | 30 |
|---|---|---|
| carboxymethylcellulose | mg | 150 |
| amide | mg | 15 |
| shellac | mg | 10 |
| sucrose | mg | 35 |
| coloring | mg | 0.5 |

The active substance is chosen from the group formed by the ganglioside derivatives described in any one of Examples 3, 4, 8 and 9.

Preparation No. 3—one gelatinous capsule contains:

| active substance | mg | 40 |
|---|---|---|
| lactose | mg | 100 |
| gastroresistant coating | mg | 5 |

The active substance is chosen from the group formed by the ganglioside derivatives described in either one of Examples 3 and 22.

Preparation No. 4—one soft gelatin capsule contains:

| active substance | mg | 50 |
|---|---|---|
| vegetable oil | mg | 200 |
| beeswax | mg | 20 |
| gelatin | mg | 150 |
| glycerin | mg | 50 |
| coloring | mg | 3 |

The active substance is chosen from the group formed by the ganglioside derivatives described in either one of Examples 3 and 22.

The following is claimed:

1. An N-acyl-N,N'-dilysoganglioside having a sphingosine and a neuraminic acid residue wherein N denotes the nitrogen atom in said sphingosine residue and N' denotes the nitrogen atom in said neuraminic acid residue, and wherein said acyl attached to N is aliphatic and having from 2 to 24 carbon atoms and being substituted in the aliphatic carbon atom chain by one to three polar groups selected from the group consisting of:

chlorine, bromine and fluorine;

free hydroxy groups or hydroxy groups esterified with an $C_1-C_6$ aliphatic acid;

$C_1-C_6$ alkyl-etherified hydroxy groups;

free carboxy groups or $C_1-C_6$ alkyl esters thereof;

free or $C_1-C_6$ alkyl substituted amino groups, and quaternary ammonium derivatives of such amino groups; and $C_1-C_6$ alkyl esters and $C_1-C_6$ alkyl amides of the sialic carboxy groups of said lysogangliosides, inner esters formed between a carboxy group in one compound and a hydroxy group in another compound of said lysogangliosides, peracylated derivatives of said lysogangliosides, metal salts, organic base salts or acid addition salts thereof.

2. An N'-acyl-N,N'-dilysoganglioside having a sphingosine and a neuraminic acid residue wherein N denotes the nitrogen atom in said sphingosine residue and N' denotes the nitrogen atom in said neuraminic acid residue, and wherein said acyl attached to N' is aliphatic and having from 2 to 24 carbon atoms and being substituted in the aliphatic carbon atom chain by one to three polar groups selected from the group consisting of:

chlorine, bromine and fluorine;

free hydroxy groups or hydroxy groups esterified with an $C_1-C_6$ aliphatic acid;

$C_1-C_6$ alkyl etherified hydroxy groups;

free carboxy groups or $C_1-C_6$ alkyl esters thereof;

free or $C_1-C_6$ alkyl substituted amino groups, and quaternary ammonium derivatives of such amino groups; and $C_1-C_6$ alkyl esters and $C_1-C_6$ alkyl amides of the sialic carboxy groups of said lysogangliosides, inner esters formed between a carboxy group in one compound and a hydroxy group in another compound of said lysogangliosides, peracylated derivatives of said lysogangliosides, metal salts, organic base salts or acid addition salts thereof.

3. An N,N'-diacyl-N,N'-dilysoganglioside having a sphingosine and a neuraminic acid residue wherein N denotes the nitrogen atom in said sphingosine residue and N' denotes the nitrogen atom in said neuraminic acid residue, and wherein said acyl attached to N and N' is derived from an unsubstituted aliphatic acyl with between 1 and 24 carbon atoms or from an aliphatic acyl with between 2 and 24 carbon atoms having one to three polar substituents in the aliphatic carbon atom chain, said polar substituents being selected from the group consisting of chlorine and fluorine;

free hydroxy groups or hydroxy groups esterified with an $C_1$-$C_6$ aliphatic acid;

$C_1$-$C_6$ alkyl etherified hydroxy groups;

free carboxy groups or $C_1$-$C_6$ alkyl esters thereof;

free or $C_1$-$C_6$ alkyl substituted amino groups, and quaternary ammonium derivatives of such amino groups; with at least one acyl group being substituted in the aforesaid manner, and $C_1$-$C_6$ alkyl esters and $C_1$-$C_6$ alkyl amides of the sialic carboxy groups of said lysogangliosides, inner esters formed between a carboxy group in one compound and a hydroxy group in another compound of said lysogangliosides, peracylated derivatives of said lysogangliosides, metal salts, organic base salts or acid addition salts thereof.

4. Acyl-di-lysogangliosides according to claim 3, in which the unsubstituted aliphatic acyl group has from 1 to 11 carbon atoms.

5. Acyl-di-lysogangliosides according to claim 4, in which the acyl group is derived from an acid selected from the group consisting of formic acid, acetic acid, propionic acid, butyric acid, valerianic acid, capronic acid, isocapronic acid, enanthic acid, caprylic acid, perlargonic acid, capric acid, undecanoic acid, tert-butylacetic acid and 2-propylvalerianic acid.

6. Acyl-lysogangliosides according to claim 4, in which the acyl group is derived from an unsaturated acid.

7. Acyl-lysogangliosides according to claims 1, 2 or 3 in which the acyl groups having from 12 to 24 carbon atoms are straight-chained.

8. Acyl-lysogangliosides according to claim 7, in which the acyl groups are having from 12 to 16 carbon atoms.

9. Acyl-lysogangliosides according to claim 8, in which the acyl groups are derived from an acid selected from the group consisting of lauric acid, myristic acid, palmitic acid, oleic acid, elaidic acid and stearic acid.

10. Acyl-lysogangliosides according to claims 1, 2 or 3, in which the acyl groups are having branched chains, in which the lateral chains are alkyls with a maximum of 4 carbon atoms.

11. Acyl-lysogangliosides according to claims 1, 2 or 3, which are derived from a ganglioside selected from the group consisting of $GM_1$, $GM_3$, $GD_{1a}$, $GD_{1b}$ and $GT_{1b}$.

12. Acyl-lysogangliosides according to claims 1, 2 or 3, in which the substituted acyl group is straight-chained and having a maximum of 12 carbon atoms.

13. Acyl-lysogangliosides according to claims 1, 2 or 3 in which the substituted acyl group is having a maximum of 12 carbon atoms and at least one branched chain, in which the lateral chains are alkyls with a maximum of 4 carbon atoms.

14. Acyl-lysogangliosides according to claims 1, 2 or 3, in which the substituted acyl group is mono-, di- or trichloro aliphatic acyl or mono-, di- or trifluoro aliphatic acyl.

15. Acyl-lysogangliosides according to claim 14, in which the substituted acyl group is having a chlorine atom in the 2-position thereof.

16. Acyl-lysogangliosides according to claim 15, in which the acyl group is dichloroacetyl, trichloroacetyl, difluoroacetyl or trifluoroacetyl.

17. Acyl-lysogangliosides according to claims 1, 2 or 3, in which the substituted acyl group is derived from a monohydroxypropionic, monohydroxybutyric or monohydroxyvalerianic acid or from their ethers on the monohydroxy groups with $C_1$-$C_6$ aliphatic alcohols or their esters on the monohydroxy group with $C_1$-$C_6$ aliphatic acids.

18. Acyl-lysogangliosides according to claim 1, in which the substituted acyl group substituting the N atom is derived from a monoacid selected from the group consisting of aminoacetic acid, 2-aminopropionic acid, 2-aminobutyric acid, 2-aminovalerianic acid, 4-aminobutyric acid and 4-aminovalerianic acid.

19. Acyl-lysogangliosides according to claims 1, 2 or 3, in which the substituted acyl group is derived from pyruvic, acetacetic or levulinic acid.

20. Acyl-lysogangliosides according to claims 1, 2 or 3, in which the substituted acyl group is derived from malonic acid, glutaric acid, maleic acid, malic acid, succinic acid, fumaric acid or their esters with $C_1$-$C_6$ aliphatic alcohols, on the carboxy group which does not take part in the acylation of the N or N' atoms.

21. Sialic carboxy esters of acyl-lysogangliosides according to claims 1, 2 or 3, which are derived from aliphatic alcohols having a maximum of 4 carbon atoms.

22. Inner esters of acyl-lysogangliosides according to claims, 1, 2 or 3, or formed by the lactonization of sialic carboxy groups with saccharide hydroxyl groups in said compounds.

23. Inner esters according to claim 22, obtained by the action of a lactonizing agent in a nonaqueous organic solvent under anhydrous conditions.

24. Inner esters according to claim 22, obtained by the action of acetic or tri-chloroacetic acid or of a carbodiimide soluble in water or in an aqueous medium.

25. Peracylated derivatives of acyl-lysogangliosides according to claims 1, 2 or 3, which are derived from aliphatic acids having a maximum of 6 carbon atoms.

26. Peracylated derivatives of acyl-lysogangliosides according to claim 25, which are derived from formic, acetic, propionic, butyric, valerianic, capronic or caprinic acid.

27. Peracylated derivatives of acyl-lysogangliosides according to claim 25, which are derived from hydroxyacids, aminoacids or dibasic acids.

28. Peracylated derivatives of acyl-lysogangliosides according to claim 25, which are derived from aromatic acids with one benzene nucleus, optionally substituted by hydroxy, amino or carboxy groups.

29. An N,N'-diacyl-N,N'-dilysoganglioside selected from the group consisting of:

N,N'-di-dichloroacetyl-di-lyso $GM_1$
N,N'-di-monochloroacetyl-di-lyso $GM_1$
N,N'-di-(3-chloropivaloyl)-di-lyso $GM_1$
N,N'-di-monohydroxyacetyl-di-lyso $GM_1$
N,N'-di-trifluoroacetyl-di-lyso $GM_1$
N,N'-di-trichloroacetyl-di-lyso $GM_1$
[N,N'-di-tribromoacetyl-di-lyso $GM_1$
N,N'-di-monomercaptoacetyl-di-lyso $GM_1$]
N,N'-di-maleyl-di-lyso $GM_1$
N,N'-di-(12-hydroxystearoyl)-di-lyso $GM_1$
N,N'-di-(2-hydroxybutyryl)-di-lyso $GM_1$ N,N'-di-monofluoroacetyl-di-lyso $GM_1$
N,N'-di-difluoroacetyl-di-lyso $GM_1$
N,N'-di-(3-aminopropionyl)-di-lyso $GM_1$
[N,N'-di-cyanoacetyl-di-lyso $GM_1$]
N,N'-di-(3-diethylaminopropionyl)-di-lyso $GM_1$ and
N,N'-di-aminoacetyl-di-lyso $GM_1$
and esters on the sialic carboxy groups, amides on the sialic carboxy groups, peracylated derivatives and alkali metal, earth alkali metal and organic base salts thereof and acid addition salts thereof.

30. N,N'-diacyl-di-lysogangliosides selected from the group consisting of:
N-dichloroacetyl-N'-acetyl-N,N'-di-lyso $GM_1$,
N-dichloroacetyl-N'-propionyl-N,N'-di lyso $GM_1$,
N-monochloroacetyl-N'-pivaloyl-N,N'-di lyso $GM_1$,
N-monohydroxyacetyl-N'-acetyl-N,N'-di lyso $GM_1$,
[N-cyanoacetyl-N'-butyryl-N,N'-di-lyso $GM_1$]
N-monofluoroacetyl-N'-palmitoyl-N,N'-di-lyso $GM_1$,
[N-mercaptoacetyl-N'-pivaloyl-N,N'-di-lyso $GM_1$]
N-trichloroacetyl-N'-formyl-N,N'-di-lyso $GM_1$,
N-3-chloropivaloyl-N'-2-propylpentanoyl-N,N'-di-lyso $GM_1$,
N-3-aminopropionyl-N'-oleyl-N,N'-di-lyso $GM_1$, and
N-aminoacetyl-N'-tert-butylacetyl-N,N'-di-lyso $GM_1$, and $C_1$–$C_6$ alkyl esters and $C_1$–$C_6$ alkyl amides on the sialic carboxy groups and peracylated derivatives of the hydroxy groups.

31. Esters of the compound set forth in claim 29 or claim 30, in which the sialic carboxy groups of said compounds are esterified with an alcohol selected from the group consisting of ethyl, propyl, isopropyl, n-butyl, isobutyl, and tert-butyl alcohols.

32. Amides of the compounds set forth in claim 29 or claim 30, in which the sialic carboxy groups of said compounds are amidated with amines selected from the group consisting of methylamine, ethylamine, propylamine, dimethylamine, and diethylamine.

33. Peracylated derivatives of the compounds according to claim 29 or 30 which are selected from the group consisting of peracetylates, perpropionylates, perbutyrylates, permaleylates, permalonylates and persuccinylates.

34. Alkali metal salts of the compounds according to claims 1, 2 or 3 which are therapeutically acceptable metal salts.

35. Alkali metal salts according to claim 34 which are sodium, potassium, ammonium, calcium, magnesium or aluminum salts.

36. Organic base salts of the compounds according to claims 1, 2 or 3 which are therapeutically acceptable organic base salts.

37. Acid addition salts of the compounds according to claim 1, 2 or 3 which are therapeutically acceptable acid addition salts.

38. A pharmaceutical composition comprising a compound according to claims 1, 2 or 3 as the active ingredient, together with a pharmaceutically acceptable excipient.

39. A pharmaceutical composition according to claim 38, in which the active ingredient is a compound selected from the group consisting of
N,N'-di-dichloroacetyl-di-lyso $GM_1$
N,N'-di-monochloroacetyl-di-lyso $GM_1$
N,N'-di-(3-chloropivaloyl)-di-lyso $GM_1$
N,N'-di-monohydroxyacetyl-di-lyso $GM_1$
N,N'-di-trifluoroacetyl-di-lyso $GM_1$
N,N'-di-trichloroacetyl-di-lyso $GM_1$
N,N'-di-maleyl-di-lyso $GM_1$
N,N'-di-(12-hydroxystearoyl)-di-lyso $GM_1$
N,N'-di-(2-hydroxybutyryl)-di-lyso $GM_1$
N,N'-di-monofluoroacetyl-di-lyso $GM_1$
N,N'-di-difluoroacetyl-di-lyso $GM_1$
N,N'-di-(3-aminopropionyl)-di-lyso $GM_1$
N,N'-di-(3-diethylaminopropionyl)-di-lyso $GM_1$
N,N'-di-aminoacetyl-di-lyso $GM_1$
N-dichloroacetyl-N'-acetyl-N,N'-di-lyso $GM_1$,
N-dichloroacetyl-N'-propionyl-N,N'-di lyso $GM_1$,
N-monochloroacetyl-N'-pivaloyl-N,N'-di lyso $GM_1$,
N-monohydroxyacetyl-N'-acetyl-N,N'-di lyso $GM_1$,
[N-cyanoacetyl-N'-butyryl-N,N'-di-lyso $GM_1$]
N-monofluoroacetyl-N'-palmitoyl-N,N'-di-lyso $GM_1$,
[N-mercaptoacetyl-N'-pivaloyl-N,N'-di-lyso $GM_1$]
N-trichloroacetyl-N'-formyl-N,N'-di-lyso $GM_1$,
N-3-chloropivaloyl-N'-2-propylpentanoyl-N,N'-di-lyso $GM_1$,
N-3-aminopropionyl-N'-oleyl-N,N'-di-lyso $GM_1$,
N-aminoacetyl-N'-tert-=butylacetyl-N,N'-di-lyso $GM_l$, and $C_1$–$C_6$ alkyl esters and $C_1$–$C_6$ alkyl amides on the sialic carboxy groups and peracylated derivatives of the hydroxy groups.

40. The N,N'-diacyl-N,N'-di-lysoganglioside according to claim 29 which is N,N'-dichloroacetyl-di-lyso-$GM_1$.

41. The pharmaceutical composition according to claim 38 comprising N,N'-di-dichloroacetyl-di-lyso $GM_1$ as the active ingredient.

* * * * *